US011220672B2

(12) United States Patent
Thomson et al.

(10) Patent No.: US 11,220,672 B2
(45) Date of Patent: Jan. 11, 2022

(54) HUMAN PLURIPOTENT STEM CELL-BASED SYSTEM FOR GENERATING ENDOTHELIAL CELLS

(71) Applicant: Wisconsin Alumni Research Foundation, Madison, WI (US)

(72) Inventors: James A. Thomson, Madison, WI (US); Jue Zhang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/986,382

(22) Filed: Dec. 31, 2015

(65) Prior Publication Data
US 2016/0186135 A1 Jun. 30, 2016

Related U.S. Application Data

(60) Provisional application No. 62/098,838, filed on Dec. 31, 2014.

(51) Int. Cl.
*C12N 5/00* (2006.01)
*C12N 5/071* (2010.01)

(52) U.S. Cl.
CPC ........ *C12N 5/069* (2013.01); *C12N 2501/115* (2013.01); *C12N 2501/15* (2013.01); *C12N 2501/155* (2013.01); *C12N 2501/16* (2013.01); *C12N 2501/415* (2013.01); *C12N 2501/727* (2013.01); *C12N 2506/45* (2013.01)

(58) Field of Classification Search
CPC ............. C12N 5/069; C12N 2501/115; C12N 2506/45; C12N 2501/155
USPC ...................................................... 435/325
See application file for complete search history.

(56) References Cited

U.S. PATENT DOCUMENTS

| | | | | |
|---|---|---|---|---|
| 9,290,741 | B2 * | 3/2016 | Palecek | C12N 5/069 |
| 2012/0295347 | A1 * | 11/2012 | Kessler | C12N 5/0692 |
| | | | | 435/366 |
| 2014/0273211 | A1 * | 9/2014 | Slukvin | C12N 5/0647 |
| | | | | 435/372 |
| 2016/0186137 | A1 | 6/2016 | Thomson et al. | |
| 2016/0186146 | A1 | 6/2016 | Thomson et al. | |
| 2016/0244728 | A1 * | 8/2016 | Hagiya | C12N 5/0696 |

OTHER PUBLICATIONS

Embryoid body definition, Wikipedia, 2017.*
James (Nature Biotech, Feb. 2010, vol. 28, No. 2, p. 161-166).*
Ludwig (Nature Methods, Aug. 2006, vol. 3, No. 8, p. 637-646).*
Prowse (Biomaterials, Nov. 2010, vol. 31, No. 32, p. 8281-8288).*
Melkoumian (Nature Biotech., Jun. 2010, vol. 28, No. 6, p. 606-610).*
Chen (Nature Methods, May 2011, vol. 8, No. 5, p. 424-429).*
Hill, "Insulin as a growth factor", Pediatric Res., 1985, vol. 19, No. 9, p. 879-886.*
Weinzimmer, J. Clin. Endocrinology & Metabolism, 2001, vol. 86, No. 4, p. 1806-1813.*
Bell, et al., Differential gene expression during capillary morphogenesis in 3D collagen matrices: regulated expression of genes involved in basement membrane matrix assembly, cell cycle progression, cellular differentiation and G-protein signaling. J Cell Sci 114, 2755-2773 (2001).
Chen et al., Chemically defined conditions for human iPSC derivation and culture, Nature Methods 8:424-429 (2011).
Chien, et al., Effects of mechanical forces on signal transduction and gene expression in endothelial cells. Hypertension 31, 162-169 (1998).
Cox, et al., Remodeling and homeostasis of the extracellular matrix: implications for fibrotic diseases and cancer. Dis. Model. Mech. 4, 165-178, doi:10.1242/dmm.004077 (2011).
Deng, et al., Endothelial RAF1/ERK activation regulates arterial morphogenesis. Blood 121, 3988-3996, doi:10.1182/blood-2012-12-474601 (2013).
Descamps, et al., Vascular differentiation from embryonic stem cells: Novel technologies and therapeutic promises. Vascul Pharmacol 56, 267-279, doi: 10.1016/j.vph.2012.03.007 (2012).
Fairbanks, et al., A Versatile Synthetic Extracellular Matrix Mimic via Thiol-Norbornene Photopolymerization. Adv Mater 21, 5005-5010 (2009).
Herbert, et al., Molecular control of endothelial cell behaviour during blood vessel morphogenesis. Nat. Rev. Mol. Cell Biol. 12, 551-564, doi:10.1038/nrm3176 (2011).
Huang, et al., Bioinformatics enrichment tools: paths toward the comprehensive functional analysis of large gene lists. Nucleic Acids Res. 37, 1-13, doi:10.1093/nar/gkn923 (2009).
Huang, et al., Systematic and integrative analysis of large gene lists using DAVID bioinformatics resources. Nat. Protocols 4, 44-57 (2009).
Hughes, et al., Matrigel: A complex protein mixture required for optimal growth of cell culture. Proteomics 10, 1886-1890, doi:10.1002/pmic.200900758 (2010).
Hughes, et al., Proteomic analysis of extracellular matrices used in stem cell culture. Proteomics 11, 3983-3991, doi:10.1002/pmic.201100030 (2011).
Ilan, et al., Distinct signal transduction pathways are utilized during the tube formation and survival phases of in vitro angiogenesis. J Cell Sci 111 ( Pt 24), 3621-3631 (1998).
James, et al., Expansion and maintenance of human embryonic stem cell-derived endothelial cells by TGF[beta] inhibition is Id1 dependent. Nat Biotech 28, 161-166 (2010).
Kleinman, et al., Matrigel: Basement membrane matrix with biological activity. Semin Cancer Biol 15, 378-386, doi:10.1016/j.semcancer.2005.05.004 (2005).

(Continued)

*Primary Examiner* — Michael C Wilson
(74) *Attorney, Agent, or Firm* — McDonnell Boehnen Hulbert & Berghoff LLP

(57) ABSTRACT

The present invention relates to chemically defined and xenogeneic material-free methods for deriving endothelial cells from human pluripotent stem cells. In particular, the present invention provides highly efficient and reproducible methods of obtaining human endothelial cells from human pluripotent stem cells, where endothelial cells derived from the methods provided herein are suitable for clinically relevant therapeutic applications.

12 Claims, 11 Drawing Sheets
(10 of 11 Drawing Sheet(s) Filed in Color)

(56) References Cited

OTHER PUBLICATIONS

Kusuma, et al., Self-organized vascular networks from human pluripotent stem cells in a synthetic matrix. Proceedings of the National Academy of Sciences 110, 12601-12606, doi:10.1073/pnas.1306562110 (2013).
Lancaster, et al., Cerebral organoids model human brain development and microcephaly. Nature 501, 373-379, doi:10.1038/nature12517 (2013).
Lei, et al., Xeno-free derivation and culture of human embryonic stem cells: current status, problems and challenges. Cell Res 17, 682-688 (2007).
Leng et al., EBSeq: an empirical Bayes hierarchical model for inference in RNA-seq experiments. Bioinformatics 29, 1035-1043, doi:10.1093/bioinformatics/btt087 (2013).
Levenberg, et al., Endothelial cells derived from human embryonic stem cells. Proc Natl Acad Sci U S A 99, 4391-4396, doi:10.1073/pnas.032074999 (2002).
Lutolf, et al., Designing materials to direct stem-cell fate. Nature 462, 433-441, doi:10.1038/nature08602 (2009).
Miyake, et al., Elastic modulus of polystyrene film from near surface to bulk measured by nanoindentation using atomic force microscopy. Appl. Phys. Lett. 89, (2006).
Moon, et al., Biomimetic hydrogels with pro-angiogenic properties. Biomaterials 31, 3840-3847, doi:10.1016/j.biomaterials.2010.01.104 (2010).
Nagase, et al., Human matrix metalloproteinase specificity studies using collagen sequence-based synthetic peptides. Biopolymers 40, 399-416 (1996).
Nakano, et al., Self-formation of optic cups and storable stratified neural retina from human ESCs. Cell Stem Cell 10, 771-785, doi:10.1016/j.stem.2012.05.009 (2012).
Nguyen, et al., Differential effects of cell adhesion, modulus and VEGFR-2 inhibition on capillary network formation in synthetic hydrogel arrays. Biomaterials 35, 2149-2161, (2014).
Niland, et al., Integrin-Mediated Cell-Matrix Interaction in Physiological and Pathological Blood Vessel Formation. Journal of Oncology 2012, 25, doi:10.1155/2012/125278 (2012).
Novosel, et al., Vascularization is the key challenge in tissue engineering. Adv. Drug Deliv. Rev. 63, 300-311 (2011).
Park et al., A comparison of human cord blood-and embryonic stem cell-derived endothelial progenitor cells in the treatment of chronic wounds, Biomaterials 34:995-1003 (2013).
Park, et al., Vascular Progenitors From Cord Blood-Derived Induced Pluripotent Stem Cells Possess Augmented Capacity for Regenerating Ischemic Retinal Vasculature. Circulation 129, 359-372, doi:10.1161/circulationaha.113.003000 (2014).
Paszek, et al., Tensional homeostasis and the malignant phenotype. Cancer Cell 8, 241-254 (2005).
Phelps, et al., Bioartificial matrices for therapeutic vascularization. Proceedings of the National Academy of Sciences, doi:10.1073/pnas.0905447107 (2009).
Phelps, et al., Engineering more than a cell: vascularization strategies in tissue engineering. Curr. Opin. Biotechnol. 21, 704-709 (2010).
Pierschbacher, et al., Cell attachment activity of fibronectin can be duplicated by small synthetic fragments of the molecule. Nature 309, 30-33 (1984).
Provenzano, et al., Matrix density-induced mechanoregulation of breast cell phenotype, signaling and gene expression through a FAK-ERK linkage. Oncogene 28, 4326-4343, (2009).
Provenzano, et al., Mechanical signaling through the cytoskeleton regulates cell proliferation by coordinated focal adhesion and Rho GTPase signaling. J. Cell Sci. 124, 1195-1205 (2011).
Ramjaun, et al., The role of cell adhesion pathways in angiogenesis. Int J Biochem Cell Biol 41, 521-530 (2009).
Salvagiotto, et al., A Defined, Feeder-Free, Serum-Free System to Generate In Vitro Hematopoietic Progenitors and Differentiated Blood Cells from hESCs and hiPSCs. PLoS One 6, doi:e17829 (2011).
Staniszewska, et al., Interaction of alpha 9 beta 1 integrin with thrombospondin-1 promotes angiogenesis. Circ Res 100, 1308-1316, doi:10.1161/01.res.0000266662.98355.66 (2007).
Stratman, et al., Endothelial Cell-Pericyte Interactions Stimulate Basement Membrane Matrix Assembly: Influence on Vascular Tube Remodeling, Maturation, and Stabilization. Microsc. microanal. 18, 68-80 (2012).
Svendsen, et al., The $\alpha 11\beta 1$ Integrin Has a Mechanistic Role in Control of Interstitial Fluid Pressure and Edema Formation in Inflammation. Arterioscler Thromb Vase Biol 29, 1864-1870, doi:10.1161/atvbaha.109.194308 (2009).
Takebe, et al., Vascularized and functional human liver from an iPSC-derived organ bud transplant. Nature 499, 481-484, doi:10.1038/nature12271 (2013).
Tulla, et al., Selective Binding of Collagen Subtypes by Integrin $\alpha 1I$, $\alpha 2I$, and $\alpha 10I$ Domains. J. Biol. Chem. 276, 48206-48212, (2001).
Velling, et al., Polymerization of Type I and III Collagens Is Dependent on Fibronectin and Enhanced by Integrins $\alpha 11\beta 1$ and $\alpha 2\beta 1$. Journal of Biological Chemistry 277, 37377-37381 (2002).
Vickerman, et al., Design, fabrication and implementation of a novel multi-parameter control microfluidic platform for three-dimensional cell culture and real-time imaging. Lab Chip 8, 1468-1477, doi:10.1039/b802395f (2008).
Vlahakis, et al., Integrin alpha 9 beta 1 directly binds to vascular endothelial growth factor (VEGF)- a and contributes to VEGF-A-induced angiogenesis. J. Biol. Chem. 282, 15187-15196, doi:10.1074/jbc.M609323200 (2007).
Vukicevic, et al., Identification of Multiple Active Growth-Factors in Basement-Membrane Matrigel Suggests Caution in Interpretation of Cellular-Activity Related To Extracellular-Matrix Components. Exp Cell Res 202, 1-8, doi:10.1016/0014-4827(92)90397-q (1992).
Wang, et al., Endothelial cells derived from human embryonic stem cells form durable blood vessels in vivo. Nat Biotechnol 25, 317-318 (2007).
White, et al., Limited Gene Expression Variation in Human Embryonic Stem Cell and Induced Pluripotent Stem Cell-Derived Endothelial Cells. Stem Cells 31, 92-103, doi:10.1002/stem.1267 (2013).
Yang, et al., Different roles of ERK and p38 MAP kinases during tube formation from endothelial cells cultured in 3-dimensional collagen matrices. J. Cell. Physiol. 200, 360-369, doi:10.1002/jcp.20025 (2004).
Yang, et al., Elastic Moduli of Collagen Gels Can Be Predicted from Two-Dimensional Confocal Microscopy. Biophys J 97, 2051-2060 (2009).
Yu, et al., FGF2 Sustains NANOG and Switches the Outcome of BMP4-Induced Human Embryonic Stem Cell Differentiation. Cell Stem Cell 8, 326-334 (2011).
Kaupisch et al., "Derivation of vascular endothelial cells from human embryonic stem cells under GMP-compliant conditions: Toward clinical studies in ischaemic disease," J. of Cardiovac Trans Res., 2012, 5:605-617.
Hayashi et al. Biological effects of culture substrates on human pluripotent stem cells, Stem Cells International, 2016.
Shibuya Vascular Endothelial Growth Factor (VEGF) and its receptor (VEGFR) signaling in angiogenesis: a crucial target for anti- and pro- angiogenic therapies, Genes & Cancer, 2011, 2(12).
Ebert et al., "Induced pluripotent stem cells from a spinal muscular atrophy patient" Nature 457(7227):277-80 (Jan. 2009). Epub Dec. 2008.
Herrmann, "Expression pattern of the Brachyury gene in whole-mount TWis/TWis mutant embryos," Development 113:913-917(1991).
Howden et al., "Genetic correction and analysis of induced pluripotent stem cells from a patient with gyrate atrophy," Proc. Natl. Acad. Sci. U.S.A. 108(16):6537-42 (Apr. 2011).
Kanayasu-Toyoda et al., "A new role of thrombopoietin enhancing ex vivo expansion of endothelial precursor cells derived from AC133-positive cells," J Biol. Chem. 282(46):33507-14 (Nov. 2007).
Langmead et al., "Ultrafast and memory-efficient alignment of short DNA sequences to the human genome," Genome Biol. 10(3):R25 (Mar. 2009) [10 pages].

(56) References Cited

OTHER PUBLICATIONS

Phelps et al., "Bioartificial matrices for therapeutic vascularization," Proc. Natl. Acad. Sci. U.S.A. 107(8): 3323-3328 (Feb. 2010).
Stewart et al., "Comparative RNA-seq Analysis in the Unsequenced Axolotl: The Oncogene Burst Highlights Early Gene Expression in the Blastema," PLoS Comput. Biol. 9(3):e1002936 (2013) [15 pages].
Tepper et al., "Adult vasculogenesis occurs through in situ recruitment, proliferation, and tubulization of circulating bone marrow-derived cells," Blood 105(3):1068-1077 (Feb. 2005).
Thomson et al., "Embryonic Stem Cell Lines Derived from Human Blastocysts," Science 282(5391):1145-1147 (Nov. 1998).
Wilkinson et al., "Expression pattern of the mouse T gene and its role in mesoderm formation," Nature 343(6259):657-659 (Feb. 1990).
Yu et al., "Induced Pluripotent Stem Cell Lines Derived from Human Somatic Cells," Science 318(5858):1917-1920 (Dec. 2007).
Yu et al., "Human induced pluripotent stem cells free of vector and transgene sequences," Science 324(5928):797-801 (May 2009).

\* cited by examiner

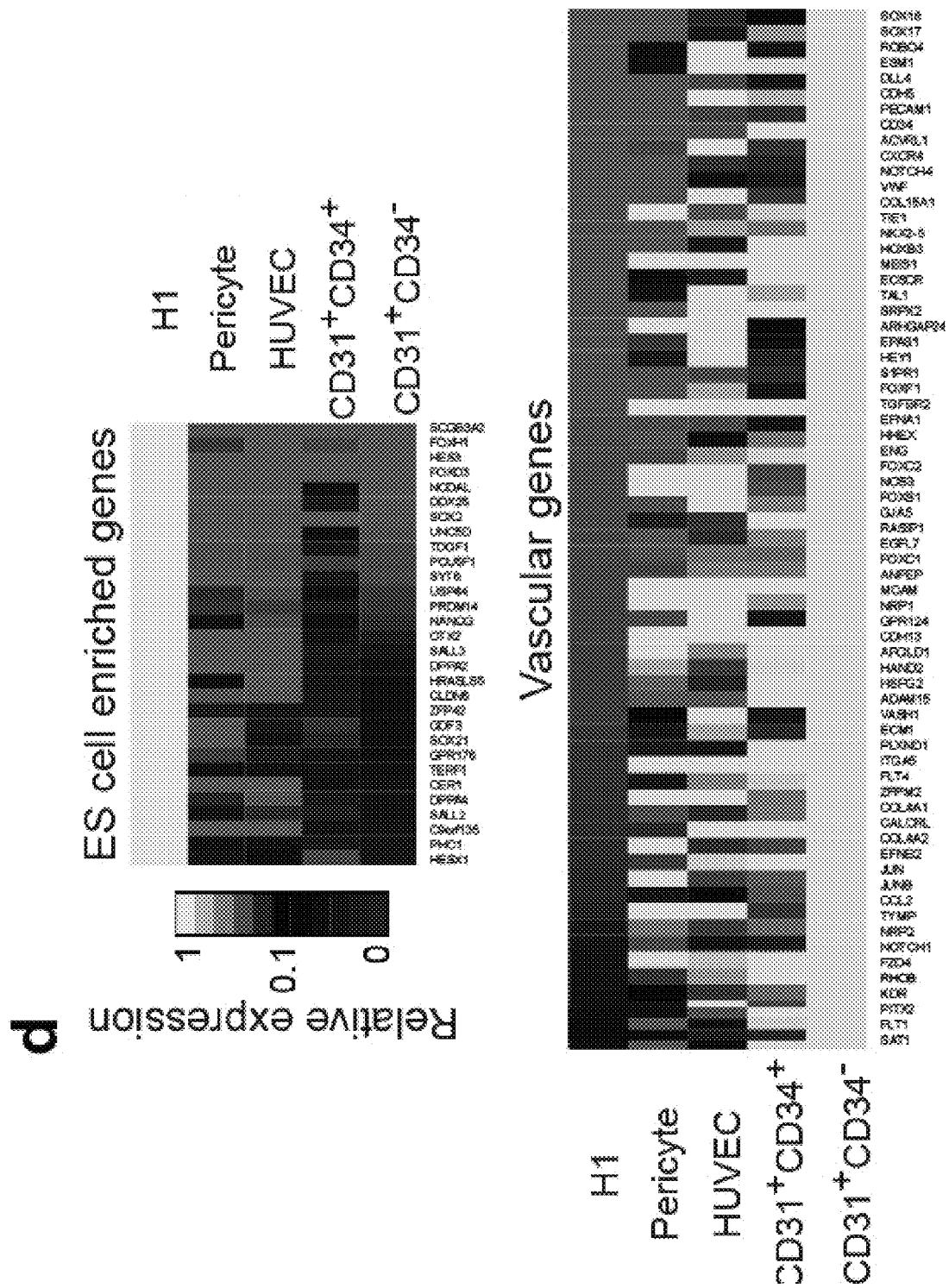
FIGS. 1A-1G, CONTINUED

FIGS. 1A-1G, CONTINUED
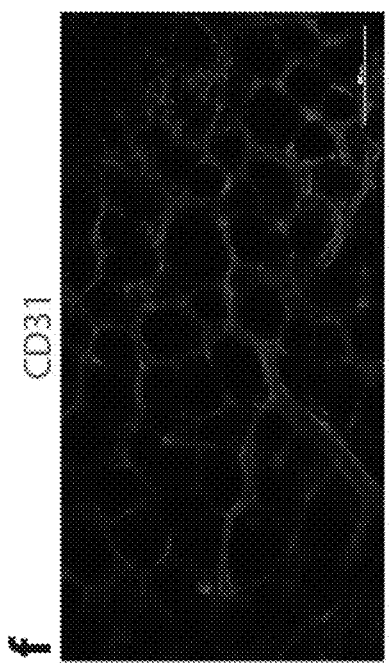
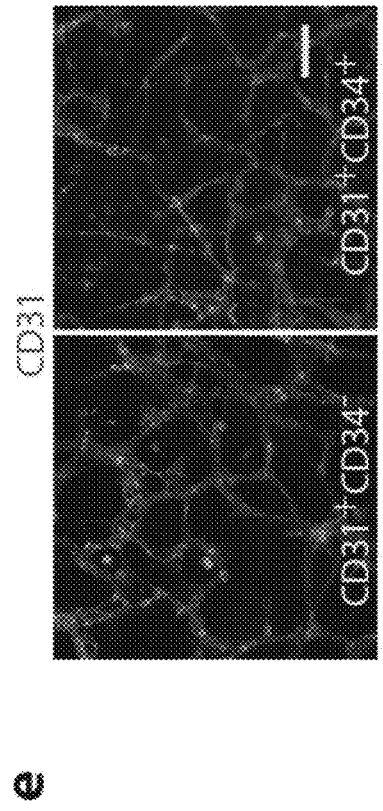
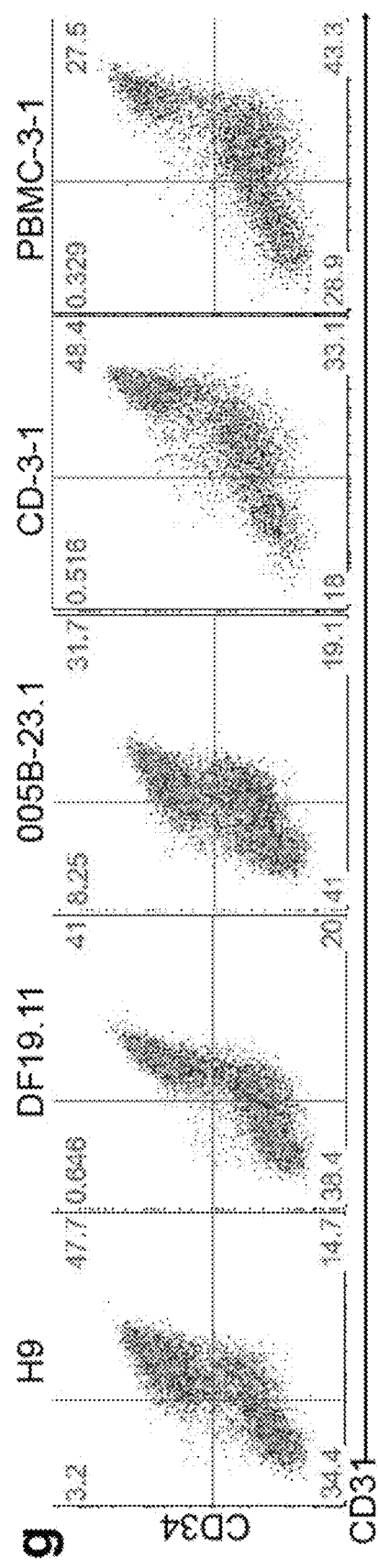

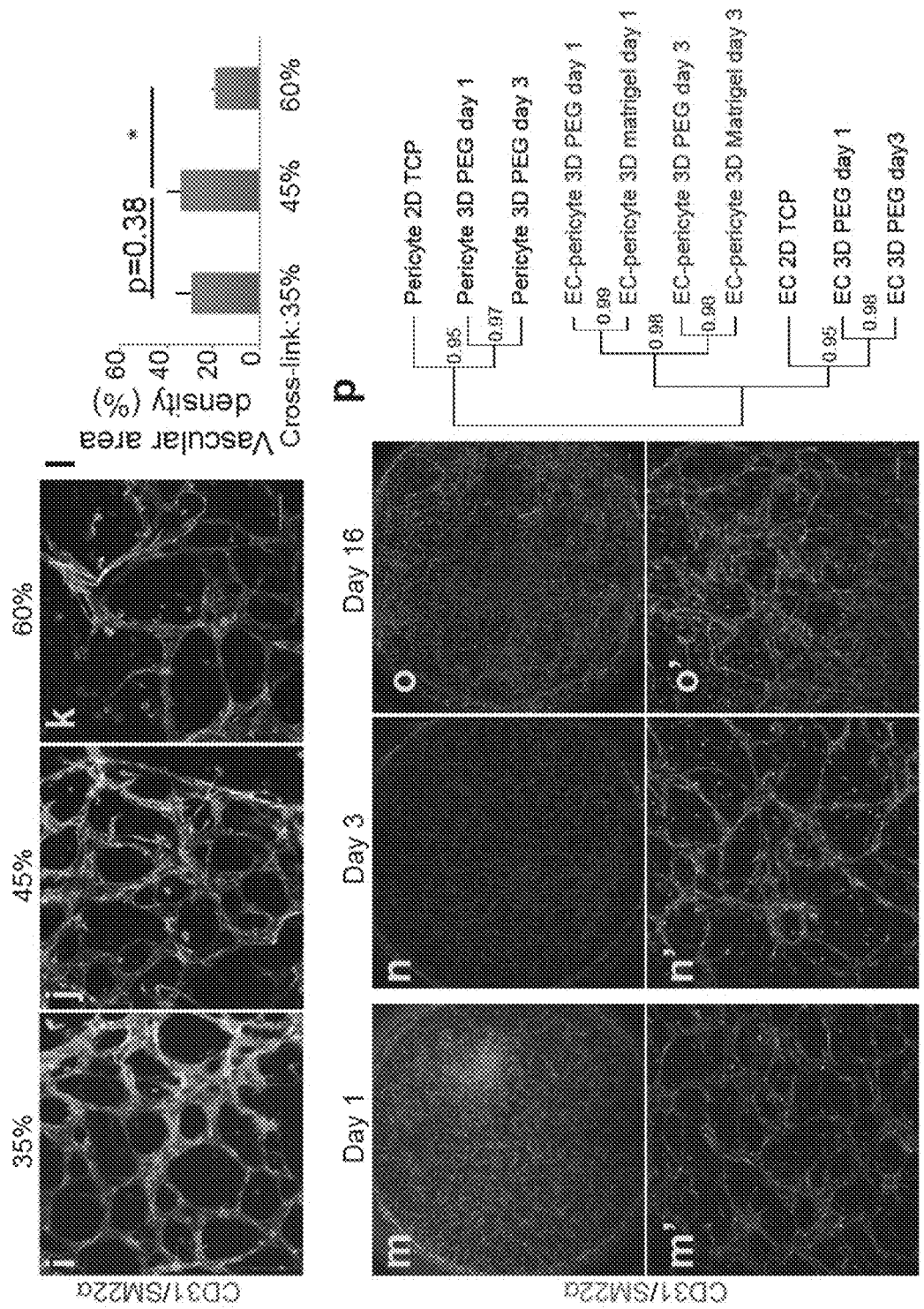
FIGS. 2A-2P, CONTINUED

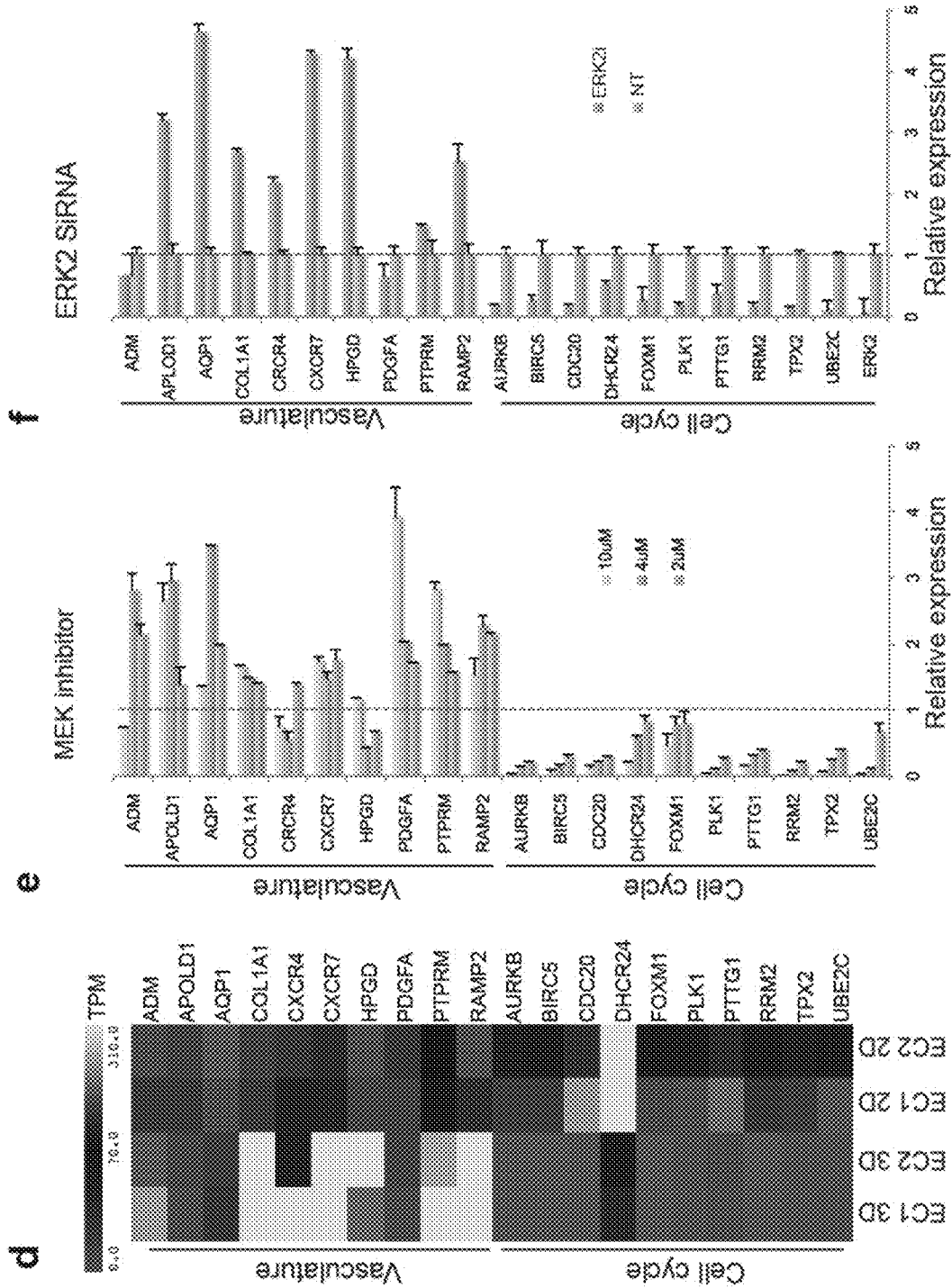
FIGS. 3A-3F, CONTINUED

HUMAN PLURIPOTENT STEM CELL-BASED SYSTEM FOR GENERATING ENDOTHELIAL CELLS

CROSS-REFERENCE TO RELATED APPLICATIONS

This application claims the benefit of U.S. Application Ser. No. 62/098,838, filed Dec. 31, 2014, which is incorporated herein as if set forth in its entirety.

STATEMENT REGARDING FEDERALLY FUNDED RESEARCH OR DEVELOPMENT

This invention was made with government support under TR000506 awarded by the National Institutes of Health. The government has certain rights in the invention.

BACKGROUND

Pluripotent stem cells offer a potentially powerful tool for improving in vitro models and investigating the underlying mechanisms of human blood vessel formation, but many challenges remain in generating human pluripotent-derived endothelial cells (ECs) suitable for large-scale use. For example, standard protocols for generating and expanding EC populations use animal-derived reagents that are often poorly defined, pose safety concerns for use in clinical applications, and contribute to highly variable results and limited reproducibility. The majority of studies have been performed in rodent models, leaving much to be desired for the study of the human cell type. There remains a need in the art, therefore, for efficient, reproducible, and xenogeneic material-free methods for differentiating human pluripotent stem cells into endothelial cells suitable for clinical cell therapies and for predictive analysis of candidate toxic agents.

SUMMARY OF THE INVENTION

In a first aspect, provided herein is a method of isolating human endothelial cells. The method comprises culturing human pluripotent stem cells to obtain a cell population comprising at least 50% CD31$^+$ endothelial cells. Culturing comprises, in order: (i) culturing the pluripotent stem cells for about two days in a chemically defined culture medium comprising a serum-free growth supplement, a Bone Morphogenetic Protein (BMP), and Activin A; and (ii) culturing the cultured cells of (i) for about three days in a chemically defined culture medium that comprises a serum-free growth supplement and does not comprise Transforming Growth Factor Beta 1 (TGFβ1), whereby the cultured cells differentiate into endothelial cells. The culture medium of (ii) can comprise one or more factors selected from the group consisting of VEGF, BMP4, BMP2, BMP7, and an inhibitor of TGFβ1-mediated signaling. The inhibitor of TGFβ1-mediated signaling can be selected from the group consisting of SB431542 and A-83-01. The cell population can comprise at least 75% CD31$^+$ endothelial cells. The cell population can comprise at least 50% CD31$^+$/CD34$^+$ endothelial cells. In some cases, the chemically defined culture medium of (i) further comprises a ROCK inhibitor. The ROCK inhibitor can be selected from the group consisting of Y27632 and Blebbistatin. The human pluripotent stem cells can be cultured in the presence of vitronectin. The vitronectin can be recombinant human vitronectin.

In another aspect, this document provides an isolated cell population of CD31+ endothelial cells obtained according to a method described herein.

In a further aspect, this document provides a method of testing a compound. The method comprises exposing the compound to a population of CD31$^+$ endothelial cells obtained according to a method described herein and examining the effect of the compound on endothelial cell growth or development.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

INCORPORATION BY REFERENCE

All publications, patents, and patent applications mentioned in this specification are herein incorporated by reference to the same extent as if each individual publication, patent, and patent application was specifically and individually indicated to be incorporated by reference.

This application includes a sequence listing in computer readable form (a "txt" file) that is submitted herewith. This sequence listing is incorporated by reference herein.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

DETAILED DESCRIPTION OF THE INVENTION

Figures 1A, 1B, 1C, 1D, 1E, 1F, 1G:
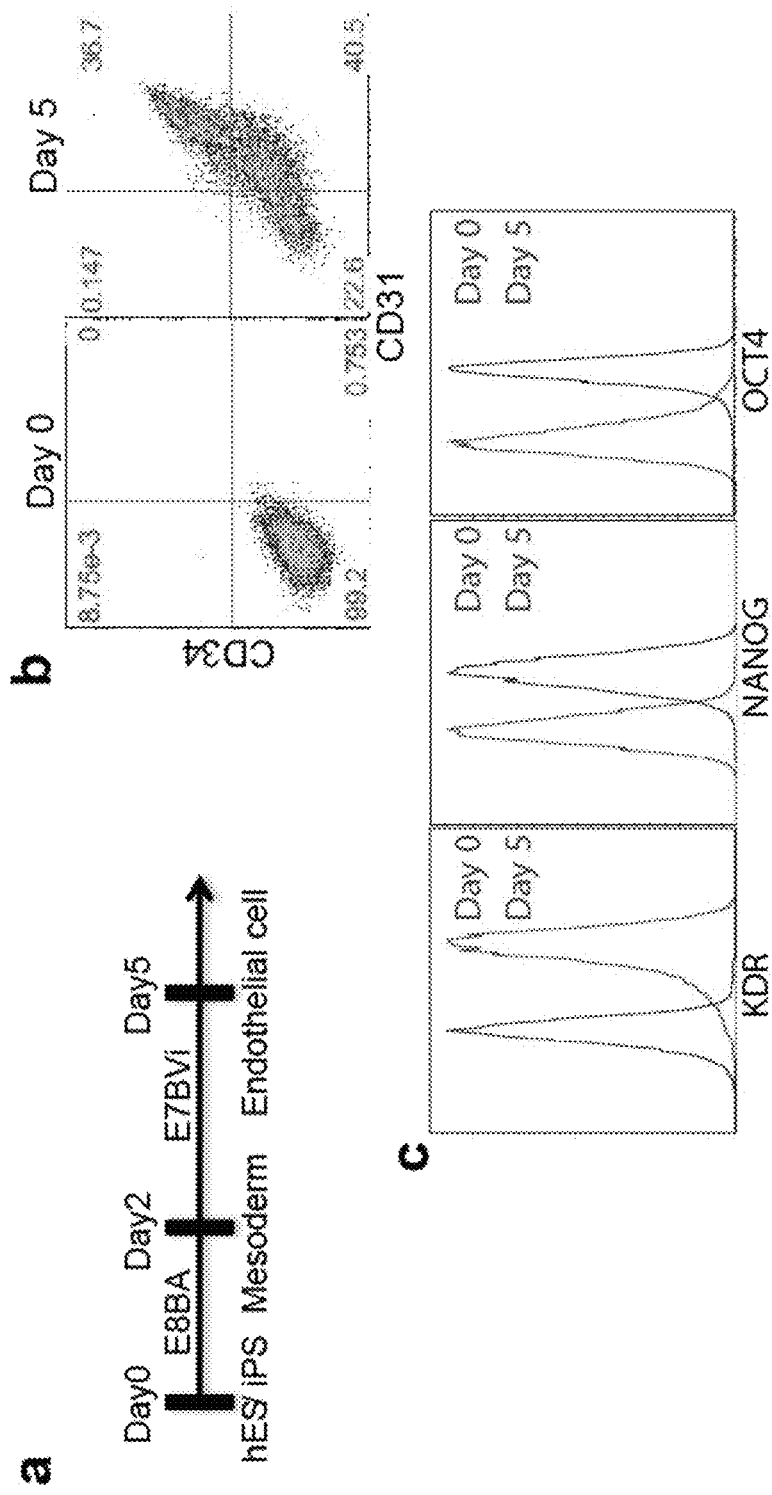
FIGS. 1A-1G demonstrate the generation and characterization of human ES- and iPS-cell derived endothelial cells. (A) Schematic of endothelial cell differentiation protocol. (B) Flow cytometric analysis of CD31 and CD34 expression at days 0 (pluripotent state) and 5 (differentiated state). (C) Flow cytometric analysis of KDR, NANOG and OCT4 expression at days 0 and 5. (D) RNA-seq analysis of H1 human ES cells, pericytes, HUVEC, CD31$^+$CD34$^-$, and CD31$^+$CD34$^+$ cells. Heat map of relative transcription levels was shown. Human ES cell enriched gene expression (TPM) was normalized to H1 human ES cells. Vascular gene expression was normalized to CD31$^+$CD34$^-$ cell. (E) In vitro Matrigel® encapsulation assay of ECs. (F) In vivo Matrigel® plug angiogenesis of CD31$^+$CD34$^-$ cells. (G) H9 human ES and four iPS cell lines were subjected to endothelial differentiation. Cells were analyzed by flow cytometry at day 5. Scale Bar: 100 µm.

Since animal-derived albumins like bovine serum albumin are xenogeneic (i.e., derived from, originating in, or being a member of a non-human species) and are known to exhibit substantial lot-to-lot variability, standard protocols for obtaining endothelial cells that require BSA yield cells that are not compatible with clinical applications for human subjects and not sufficiently uniform for in vitro applications such as drug screening and modeling human development or disease. The present invention is based at least in part on the Inventors' discovery of BSA-free, xenogeneic material-free ("xeno-free") protocols for differentiating human pluripotent stem cells into endothelial cells under chemically defined conditions. In particular, populations of $CD31^+$ endothelial cells (ECs) were generated from both human embryonic stem cells (human ES cells) and induced pluripotent stem cells (human iPS cells) using xeno-free, chemically-defined protocols. Based on these discoveries, the present invention provides fully defined and xeno-free methods of producing and expanding clinically relevant human endothelial cells for clinical cell therapies and tissue modelling applications. In particular, the present invention provides a fully defined and xeno-free method of producing and expanding clinically relevant human endothelial cells for clinical cell therapies and tissue modelling applications. Accordingly, the compositions and methods described herein also provide a unique opportunity to study these cells in a three-dimensional human tissue construct.

In a first aspect, therefore, the present invention provides a method of generating endothelial cells. The method comprises differentiating human pluripotent stem cells under xenogen-free, chemically defined (i.e., in the presence of a chemically defined medium) conditions that promote differentiation to endothelial cells. In exemplary embodiments, differentiating comprises culturing human pluripotent stem cells in a chemically defined culture medium comprising a serum-free growth supplement and one or more endothelial cell differentiating factors, whereby a cell population comprising human $CD31^+$ endothelial cells is obtained.

According to methods of the present invention, human pluripotent cells are cultured in a chemically defined culture medium comprising a serum-free growth supplement. As used herein, the terms "chemically defined medium" and "chemically defined culture medium" are used interchangeably and refer to formulations of biochemically-defined constituents that can include constituents of known chemical composition. As used herein, the terms "chemically defined medium" and "chemically defined cultured medium" also refer to a culture medium containing formulations of fully disclosed or identifiable ingredients, the precise quantities of which are known or identifiable and can be controlled individually. As such, a culture medium is not chemically defined if (1) the chemical and structural identity of all medium ingredients is not known, (2) the medium contains unknown quantities of any ingredients, or (3) both. Standardizing culture conditions by using a chemically defined culture medium minimizes the potential for lot-to-lot or batch-to-batch variations in materials to which the cells are exposed during cell culture. Accordingly, the effects of various differentiation factors are more predictable when added to cells and tissues cultured under chemically defined conditions. As used herein, the term "serum-free" refers to cell culture materials that are free of serum obtained from animal (e.g., fetal bovine) blood. Culturing cells or tissues in the absence of animal-derived materials (i.e., under xenogen-free conditions) reduces or eliminates the potential for such cross-species viral or prion transmission. As used herein, the terms "xenogen-free" and "xeno-free" are used interchangeably and refer to cell or tissue culture conditions that avoid the use of xenogeneic materials including, without limitation, animal-derived cells, exudates, or other constituents of animal (e.g., non-human) origin. As used herein, the term "xeno-free" also refers to a medium free of any cell or cell product of a species other than that of the cultured cell. Human proteins are preferred but not essential for chemically defined conditions, provided that uncharacterized animal products are excluded.

In exemplary embodiments, a method of the present invention provides comprises differentiating human pluripotent stem cells under xenogen-free, chemically defined conditions (i.e., in the presence of a chemically defined medium), whereby the pluripotent stem cells differentiate into cells having an early mesoderm phenotype. As used herein, "an early mesoderm phenotype" includes expression of brachyury, which is considered to be one of the best markers of mesoderm cells and is used to track the development of the mesodermal lineage. Brachyury is expressed transiently in all cells ingressing through the primitive streak as well as in the nascent and early migrating mesoderm. Wilkinson et al., *Nature* 343:657-9 (1990); Herrmann et al., *Development* 113:913-7 (1991). Other markers of an early mesoderm phenotype include, without limitation, FoxF1, GATA4, Isl1, Tbx20, PDGFR-alpha, and PDGFR-beta. As used herein, "mesodermal cells" refers to reference to mesodermal-like cells or cells which are committed to differentiate into mesodermal cells. Reference herein to "mesodermal cells" includes any cell of mesodermal lineage such as mesendoderm, extraembryonic mesoderm and embryonic mesoderm, as well as their partially or terminally differentiated progenitors.

Preferably, human pluripotent stem cells are cultured in a chemically-defined basal culture medium formulation comprising the defined components of culture medium "DF3 S" as set forth in Chen et al., *Nature Methods* 8:424-429 (2011), which is incorporated by reference herein as if set forth in its entirety. As used herein, the terms "E7 culture medium" and "E7" are used interchangeably and refer to a chemically defined culture medium comprising or consisting essentially of DF3S supplemented to further comprise insulin (20 µg/mL), transferrin (10.67 ng/mL) and human Fibroblast Growth Factor 2 (FGF2) (100 ng/mL). As used herein, the terms "E8 culture medium" and "E8" are used interchangeably and refer to a chemically defined culture medium comprising or consisting essentially of DF3S supplemented by the addition of insulin (20 µg/mL), transferrin (10.67 ng/mL), human FGF2 (100 ng/mL), and human TGFβ1 (Transforming Growth Factor Beta 1) (1.75 ng/mL).

In exemplary embodiments, human pluripotent stem cells are cultured for about two days in the presence of a serum-free, chemically-defined culture medium that is supplemented to further comprise bone morphogenetic protein 4 (BMP4) and Activin-A. As used herein, the term "E8BA medium" refers to an E8 medium supplemented to comprise BMP4 and Activin A. In some cases, the chemically defined culture medium further comprises a Rho kinase (ROCK) inhibitor selected from the group consisting of Y-27632, Blebbistatin (a selective and high-affinity small molecule inhibitor of myosin heavy chain ATPase), and HA1077 (fasudil).

In some cases, the method further comprises culturing the cells in a serum-free, chemically defined culture medium that does not comprise TGFβ1. For example, cells can be further cultured in the presence of a chemically-defined culture medium comprising or consisting essentially of the following defined components: DMEM-F12, NaHCO$_3$, L-Ascorbic Acid, selenium, transferrin, insulin, and FGF2. In exemplary embodiments, human pluripotent stem cells are cultured in the presence of an E7 defined medium supplemented to further comprise VEGFA ("E7V medium") or to comprise VEGFA, a bone morphogenetic protein (e.g., BMP4, BMP2, or BMP7), and an inhibitor of TGFβ1-mediated signaling (e.g., SB431542, A-83-01) ("E7BVi medium" or "E7BVi").

In some cases, a method of the invention comprises culturing human pluripotent stem cells in a medium comprising or consisting essentially of the following defined components: DMEM/F12, L-ascorbic acid-2-phosphate magnesium (64 mg/l), sodium selenium (14 µg/l), FGF2 (100 µg/l), insulin (20 mg/l), NaHCO$_3$ (543 mg/l), transferrin (10.7 mg/l), TGFβ1 (2 BMP-4 (5 µg/l), and Activin-A (25 µg/l). In other cases, the method further comprises culturing the pluripotent stem cells in a medium comprising or consisting essentially of the following defined components: DMEM/F12, L-ascorbic acid-2-phosphate magnesium (64 mg/l), sodium selenium (14 µg/l), FGF2 (100 µg/l), insulin (20 mg/l), NaHCO$_3$ (543 mg/l), transferrin (10.7 mg/l), and VEGFA (50 µg/l).

In yet other cases, a method of the invention comprises culturing human pluripotent stem cells in a medium comprising or consisting essentially of the following defined components: DMEM/F12, L-ascorbic acid-2-phosphate magnesium (64 mg/l), sodium selenium (14 µg/l), FGF2 (100 µg/l), insulin (20 mg/l), NaHCO$_3$ (543 mg/l), transferrin (10.7 mg/l), VEGFA (50 µg/l), BMP4 (50 µg/l), and SB431542 (5 µM). In some cases, BMP2 or BMP7 is used in place of BMP4. In some cases, the inhibitor of TGFβ1-mediated signaling A-83-01 is used in place of SB431542.

CD31 is an antigenic marker for mature endothelial cells lining the lumen of blood vessels (Tepper et al., *Blood* 105:1068-1077 (2005)) and serves as an early indicator of endothelial differentiation (Kanayasu-Toyoda et al., *J. Biol. Chem.* 282:33507-14 (2007)). Endothelial progenitor cells mature into CD31$^+$ endothelial cells. Accordingly, endothelial cells obtained according to a method of the present invention have one of the following expression profiles: CD31$^+$/CD34$^+$ and CD31$^+$/CD34$^-$. Human CD31$^+$/CD34$^+$ cells have been shown to form networks of capillary-like structures when seeded on Matrigel (Wang et al., *Nature Biotechnology* 24(3):317-8 (2007)). Cell populations obtained by a method of the present invention comprise at least 30% (e.g., at least 30%, 40%, 50%, 60%, 70%, 80%, 90%, 95%, or more) CD31-positive ("CD31$^+$") cells. Following an additional 3 days in culture, CD31$^+$/CD34$^-$ endothelial cells differentiate into CD31$^+$CD34$^+$ cells. Endothelial cells derived from ES cells differ from circulating EPCs in that human ES cell-derived ECs secrete significantly higher levels of cytokines VEGF and Ang-1 as compared to EPCs obtained from human cord blood, and also demonstrate significantly accelerated re-epithelialization and wound healing in a wound model as compared to circulating EPCs (Park et al., *Biomaterials* 34:995-1003 (2013)).

As used herein, "pluripotent stem cells" appropriate for use according to a method of the invention are cells having the capacity to differentiate into cells of all three germ layers. Suitable pluripotent cells for use herein include human ES cells and human induced pluripotent stem cells (iPS cells). As used herein, "embryonic stem cells" or "ES cells" mean a pluripotent cell or population of pluripotent cells derived from an inner cell mass of a blastocyst. See Thomson et al., *Science* 282:1145-1147 (1998). These cells express at least Oct-4, SSEA-3, SSEA-4, TRA-1-60, or TRA-1-81, and appear as compact colonies having a high nucleus to cytoplasm ratio and prominent nucleolus. ES cells are commercially available from sources such as WiCell Research Institute (Madison, Wis.). As used herein, "induced pluripotent stem cells" or "iPS cells" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ES cells, as described herein. See, e.g., Yu et al., *Science* 318:1917-1920 (2007).

iPS cells exhibit morphological properties (e.g., round shape, large nucleoli and scant cytoplasm) and growth properties (e.g., doubling time of about seventeen to eighteen hours) akin to ES cells. In addition, iPS cells express pluripotent cell-specific markers (e.g., Oct-4, SSEA-3, SSEA-4, Tra-1-60 or Tra-1-81, but not SSEA-1). iPS cells, however, are not immediately derived from embryos. As used herein, "not immediately derived from embryos" means that the starting cell type for producing iPS cells is a non-pluripotent cell, such as a multipotent cell or terminally differentiated cell, such as somatic cells obtained from a post-natal individual.

In another aspect, the present invention provides methods for obtaining xenogen-free endothelial cells derived from a particular mammalian subject (e.g., a particular human subject). For example, it may be advantageous to obtain endothelial cells that exhibit one or more specific phenotypes associated with or resulting from a particular disease or disorder of the particular mammalian subject. In some cases, subject-specific cells for use in a neural construct of the invention are induced pluripotent stem cells obtained by reprogramming somatic cells of an individual human subject according to methods known in the art. See, for example, Yu et al., *Science* 324(5928):797-801 (2009); Chen et al., *Nat Methods* 8(5):424-9 (2011); Ebert et al., *Nature* 457(7227): 277-80 (2009); Howden et al., *Proc Natl Acad Sci USA* 108(16):6537-42 (2011). Human induced pluripotent stem cell-derived endothelial cells allow modeling of drug responses in tissue constructs that recapitulate neural or other tissue in an individual having, for example, a particular disease. Even the safest drugs may cause adverse reactions in certain individuals with a specific genetic background or environmental history. Accordingly, iPS cell-derived endothelial cells obtained according to methods of the present invention from individuals having known susceptibilities or resistances to various drugs or diseases will be useful in identifying genetic factors and epigenetic influences that contribute to variable drug responses.

Subject-specific somatic cells for reprogramming into induced pluripotent stem cells can be obtained or isolated from a target tissue of interest by biopsy or other tissue sampling methods. In some cases, subject-specific cells are manipulated in vitro prior to use in a neural construct of the invention. For example, subject-specific cells can be expanded, differentiated, genetically modified, contacted to polypeptides, nucleic acids, or other factors, cryo-preserved, or otherwise modified prior to use in a neural construct of the present invention.

In some cases, endothelial cell populations obtained according to a method of the present invention are combined with other cell types to obtain various endothelial cell-derived or endothelial cell-associated cells and tissues. For example, endothelial cells obtained according to a method of the present invention can be provided with vascular smooth muscle cells to promote blood vessel formation in a three-dimensional hydrogel-based tissue construct as described in U.S. application Ser. No. 14/986,363 and U.S. application Ser. No. 14/986,224, which are incorporated herein as if set forth in their entirety. Endothelial cells and mesenchymal cells contribute to an interconnected vasculature within the tissue construct. Isolated endothelial cells and endothelial cell populations generated from hPSCs according to the methods provided herein will be beneficial for many potential applications such as engineering new blood vessels, endothelial cell transplantation into the heart for myocardial regeneration, induction of angiogenesis for treatment of regional ischemia, and screening for drugs affecting vasculature such as angiogenesis inhibition to slow cancer progression.

In exemplary embodiments, human pluripotent stem cells (e.g., human ES cells or iPS cells) are cultured in the absence of a feeder layer (e.g., a fibroblast layer) and in the presence of a chemically defined, xenogen-free substrate. For example, human pluripotent cells can be cultured in the presence of a substrate comprising vitronectin, a vitronectin fragment or variant, a vitronectin peptide, a self-coating substrate such as Synthemax® (Corning), or combinations thereof. In exemplary embodiments, the chemically-defined, xeno-free substrate is a plate coated in recombinant human vitronectin peptides or polypeptides (e.g., recombinant human vitronectin).

The expression of a number of cell type-associated markers (or the lack thereof) can be used to characterize endothelial cells obtained according to the methods provided herein. For example, the expression of some markers associated with pluripotency in hPSCs decline over the course of differentiation of the hPSCs into the endothelial lineage. Such pluripotency markers include Oct4, Nanog, SSEA-3, SSEA-4, TRA-1-60, and TRA-1-81.

Suitable methods for detecting the presence or absence of biological markers are well known in the art and include, without limitation, immunohistochemistry, qRT-PCR, RNA sequencing, and the like for evaluating gene expression at the RNA level. For example, a cell population obtained according to a method provided herein can be evaluated for expression of biological markers of endothelial cells. RT-PCR is useful to verify the expression of known endothelial cell (EC) markers including CD31 (PECAM), CD34, CD144 (VE-cadherin), and Von Willebrand factor (vWF). In some cases, endothelial phenotypes of such cells can be evaluated using immunofluorescence staining for a variety of EC surface antigens such as, without limitation, human CD34, CD31, and KDR (VEGF receptor). Quantitative methods for evaluating expression of markers at the protein level in cell populations are also known in the art. For example, flow cytometry is used to determine the fraction of cells in a given cell population that express or do not express biological markers of interest (e.g., CD31, CD34).

As described in the Examples section below, differentiation of human pluripotent stem cells into ECs according to methods of the present invention can be confirmed based on expression of endothelial cell markers (e.g., CD31, CD34, CD144/CDH5/VE-cadherin). Endothelial cell identity is also associated with upregulation of KDR/VEGFR2 gene expression, upregulation of vasculogenesis and angiogenesis markers, and downregulation of pluripotency markers such as NANOG and OCT4 (relative to human ES cells or induced pluripotent stem cells). Silencing of pluripotency markers was observed in both CD31+CD34− and CD31+ CD34+ cell populations compared to H1 ES cells.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

As used herein, "a medium consisting essentially of" means a medium that contains the specified ingredients and those that do not materially affect its basic characteristics.

As used herein, "serum-free" means that a medium does not contain serum or serum replacement, or that it contains essentially no serum or serum replacement. Likewise, an "albumin free" culture medium means a medium that does not contain albumin or is essentially free of albumin. As used herein, "effective amount" means an amount of an agent sufficient to evoke a specified cellular effect according to the present invention.

As used herein, the term "about" means within 5% of a stated concentration range, density, temperature, or time frame.

The invention will be more fully understood upon consideration of the following non-limiting Examples. It is specifically contemplated that the methods disclosed are suited for pluripotent stem cells generally. All papers and patents disclosed herein are hereby incorporated by reference as if set forth in their entirety.

EXAMPLES

Example 1—Endothelial Cell Differentiation Under Xeno-Free Conditions

Materials and Methods

Reagents: Anti-CD31-PE (BD PharMingen, clone WM-59), Anti-CD34-APC (BD PharMingen, clone 581), Anti-CD31 (Dako, cat #M0823), Anti-VE-cadherin (BD Pharmingen, cat #555661), Anti-SM22α (Abcam, cat #ab14106), acetylated low-density lipoprotein (LDL-FITC, Invitrogen). Batch 1 BSA (Fisher Scientific, cat #BP1606, lot 106563), Batch 2 BSA (Sigma, cat #A7906, lot 069K1653), batch 3 BSA (Sigma, cat #A9647, lot 071M1487V), Batch 4 BSA (Miltenyi Biotec, cat #130-091-376, lot 5120309144), Batch 5 BSA (Sigma, cat #2153, lot 066K0738), Batch 6 BSA (Sigma, cat #A9418), and Batch 7 BSA (Sigma, cat #A9576, lot SLBB5246). Note: the manufacturer labels Batch 6 and 7 BSA with "suitable for cell culture," but Batch 5 (and not Batches 6 and 7) supported cell survival during EC differentiation.

Human ES/iPS Cell Culture: All human ES/iPS cells were maintained in E8 medium on Matrigel®-coated tissue culture plates, and were passaged routinely with EDTA as described previously (Chen et al., Nature Methods 8(5): 424-9 (2011)). Cell line 005B23.1 was derived from skin punch fibroblast and maintained on recombinant human vitronectin-coated plates. Cell line DF19.11 was derived from foreskin fibroblast. Cell line CD-3-1 was derived from cord blood cell. PBMCs were peripheral blood mononuclear cells.

Endothelial cell differentiation, purification, and culture: 80-90% confluence ES/iPS cells were dissociated by TrypLE (Invitrogen) for 3 minutes at 37° C. Cells were plated on vitronectin-coated plate (comprising recombinant vitronectin, 60 µg/plate) at 1:3 ratios (1 to $1.5 \times 10^5$ cells/cm$^2$). 10 µM Y27632 (ROCK inhibitor) was used on the first day to improve cell survival. Cells were cultured in E8BA or E8BAC (E8BA supplemented with 1 µM CHIR99021) (used in FIG. 2) for two days and then switched to E7BVi or other medium (used in FIG. 2) for another three days. To isolate CD31$^+$CD34$^+$ cells, cells were labeled with CD34 magnetic beads and processed through autoMACS (Miltenyi Biotec). To isolate CD31$^+$CD34$^-$ cells, the side population from above was further labeled with CD31 beads and purified by autoMACS. Purified CD31$^+$CD34$^-$ cells were cultured on fibronectin-coated plate with E7V medium.

Depending on the cell line, cell populations comprising 50%-90% endothelial cells were achieved by day 5. Endothelial cell differentiation can be induced by E7Vi, E7Bi, E7, or E6V medium. E7Bi medium mainly induced CD31$^+$CD34$^-$ cells, while E7V and E7Vi mainly induced CD31$^+$/CD34$^+$ cell differentiation.

TABLE 1

Chemically Defined Cell Medium Components

| Medium | Chemically Defined Components |
|---|---|
| E8 | DMEM/F12; L-ascorbic acid-2-phosphate magnesium (64 mg/l); sodium selenium (14 µg/l); human FGF2 (100 µg/l); insulin (20 mg/l); NaHCO$_3$ (543 mg/l); transferrin (10.7 mg/l); TGFβ1 (2 µg/l) |
| E8BA | E8 medium + 5 µg/l BMP4 and 25 µg/l Activin A |
| E7 | DMEM/F12; L-ascorbic acid-2-phosphate magnesium (64 mg/l); sodium selenium (14 µg/l); human FGF2 (100 µg/l); insulin (20 mg/l); NaHCO$_3$ (543 mg/l); and transferrin (10.7 mg/l) |
| E7BVi | E7 medium + 50 µg/l VEGF + 50 µg/l BMP4 + 5 µM SB431542 |
| E7Bi | E7 medium + 50 µg/l BMP4 + 5 µM SB431542 |
| E7Vi | E7 medium + 50 µg/l VEGF + 5 µM SB431542 |
| E6 | DMEM/F12; L-ascorbic acid-2-phosphate magnesium (64 mg/l); sodium selenium (14 µg/l); insulin (20 mg/l); NaHCO$_3$ (543 mg/l); and transferrin (10.7 mg/l) |
| E6V | E6 medium + 50 µg/l VEGF |

3D Matrigel® encapsulation assay: $1.5 \times 10^6$ endothelial cells/ml and $0.75 \times 10^6$ pericytes/ml (ScienCell, cat #1200) were encapsulated in 5 mg/ml Matrigel®. A 10 µL monomer/cell solution was spotted in the middle of 24-well plate and incubated for 5 minutes at 37° C. for solidification. E7V medium was then applied. Immunostaining was performed on day 4 and the structures were imaged using confocal microscopy.

In vivo Matrigel® plug angiogenesis assay: $5 \times 10^5$ endothelial cells were resuspended in 100 µl E7V medium and 200 µL Matrigel. A 300 µL cell Matrigel mixture was subcutaneously injected into the neck of nude mice. After inoculation for two weeks, the injected plug was harvested, fixed, and immunostained.

RNA-sequencing and data processing: Total RNA was isolated by RNeasy Kit (Qiagen). A cDNA library was prepared by Illumina TruSeq protocol and sequenced by HiSeq 2500. Data processing was performed as previously described. See Stewart et al., PLoS Comput. Biol. 9:e1002936 (2013). Briefly, FASTQ files of nucleotide sequence were generated by CASAVA (v1.8.2) and reads were mapped to human transcriptome (hg19, v1.1.17) with Bowtie (v0.12.8) (Langmead et al., Genome Biol. 10:R25 (2009)). The gene expression was calculated by RSEM (RNA-seq by Expectation-Maximization) (v1.1.21).

Results and Discussion

Previous protocols for deriving ECs have been difficult to reproduce and often require biological components derived from animal sources that are poorly defined. Descamps et al., Vascul. Pharmacol. 56:267-279 (2012). Therefore, we derived endothelial cells using defined conditions, including recombinant vitronectin for surface coating, xeno-free differentiation medium, and no bovine serum albumin (BSA). Using our BSA-free and xeno-free protocol, we explored the influence of materials on human vasculogenesis by using synthetic hydrogels with adaptable biochemical and mechanical properties.

Figures 4A, 4B, 4C:
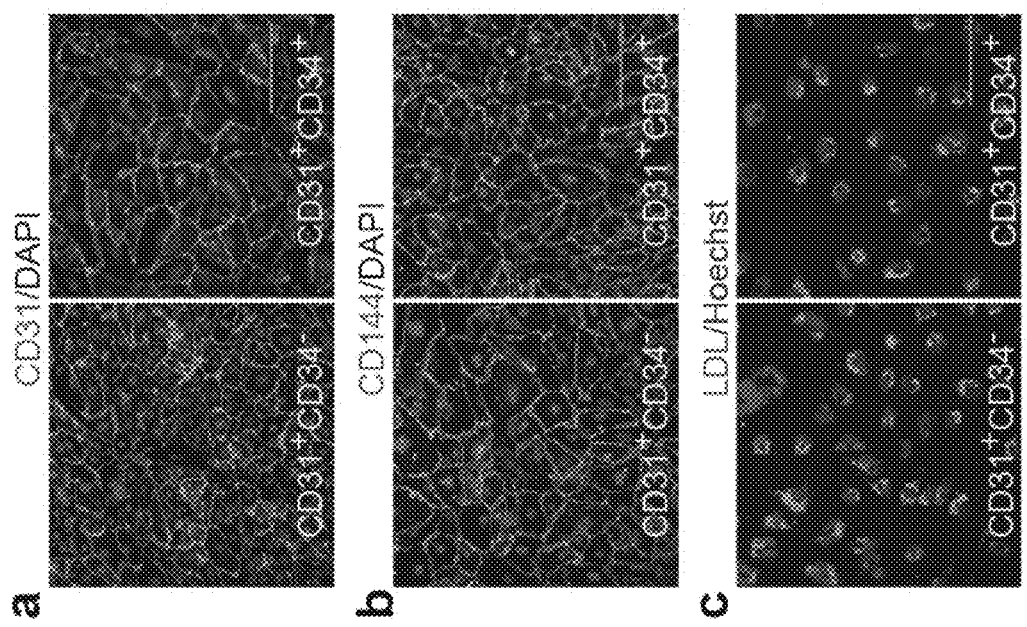
FIGS. 4A-4C are images of marker expression in endothelial cells. (A, B) Immunostaining was performed to characterize CD31 and CD144 expression of purified endothelial cells. (C) LDL uptake assay. Scale Bar: 100 μm. Anti-CD31-PE (BD PharMingen, clone WM-59), Anti-CD34-APC (BD PharMingen, clone 581), Anti-CD31 (Dako, cat #M0823), Anti-VE-cadherin (BD Pharmingen, cat #555661), Anti-SM22α (Abcam, cat #ab14106), acetylated low-density lipoprotein (LDL-FITC, Invitrogen).

We developed a defined 3D model for blood vessel formation in which human pluripotent stem cell-derived endothelial cells (ECs) are cultured within synthetic extracellular matrices (sECM). ECs (50%-80% CD31$^+$ cells; six separate cell lines) were derived from both embryonic stem cells (ESCs) and induced pluripotent stem cells (iPSCs)

using our xeno-free, chemically-defined protocol: human pluripotent stem cells were first differentiated into cells having mesoderm identity using BMP4 and Activin-A (E8BA medium) for two days. These mesoderm cells were then treated with BMP4, VEGFA, and SB431542 (a TGF-β receptor inhibitor) (E7BVi medium) for another three days, yielding both $CD31^+CD34^-$ and $CD31^+CD34^+$ EC populations (FIGS. 1a-b). EC fate was further confirmed by upregulation of KDR/VEGFR2 and downregulation of NANOG and OCT4 (FIG. 1c). Silencing of other ESC enriched genes was observed in both $CD31^+CD34^-$ and $CD31^+CD34^+$ cell populations compared to H1 ESCs (FIG. 1d). Vasculogenesis/angiogenesis genes for both EC populations were upregulated (FIG. 1d). Furthermore, ECs expressed endothelial markers CD144 (CDH5/VE-cadherin), internalized LDL (FIG. 4), and formed capillary networks in vitro and in vivo (FIGS. 1e-f). Importantly, our protocol generated 50-80% $CD31^+$ endothelial cells from two ESC (H1 and H9) and four iPSC (DF19.11, CD-3-1, PBMC-3-1, and 005B-23.1) sources (FIG. 1g), including an iPSC (005B-23.1) line that was established using chemically defined xeno-free conditions. Therefore, these data demonstrate robust and efficient generation of human ECs in chemically defined conditions, thus addressing a crucial production requirement for potential clinical applications.

Figures 2A, 2P:
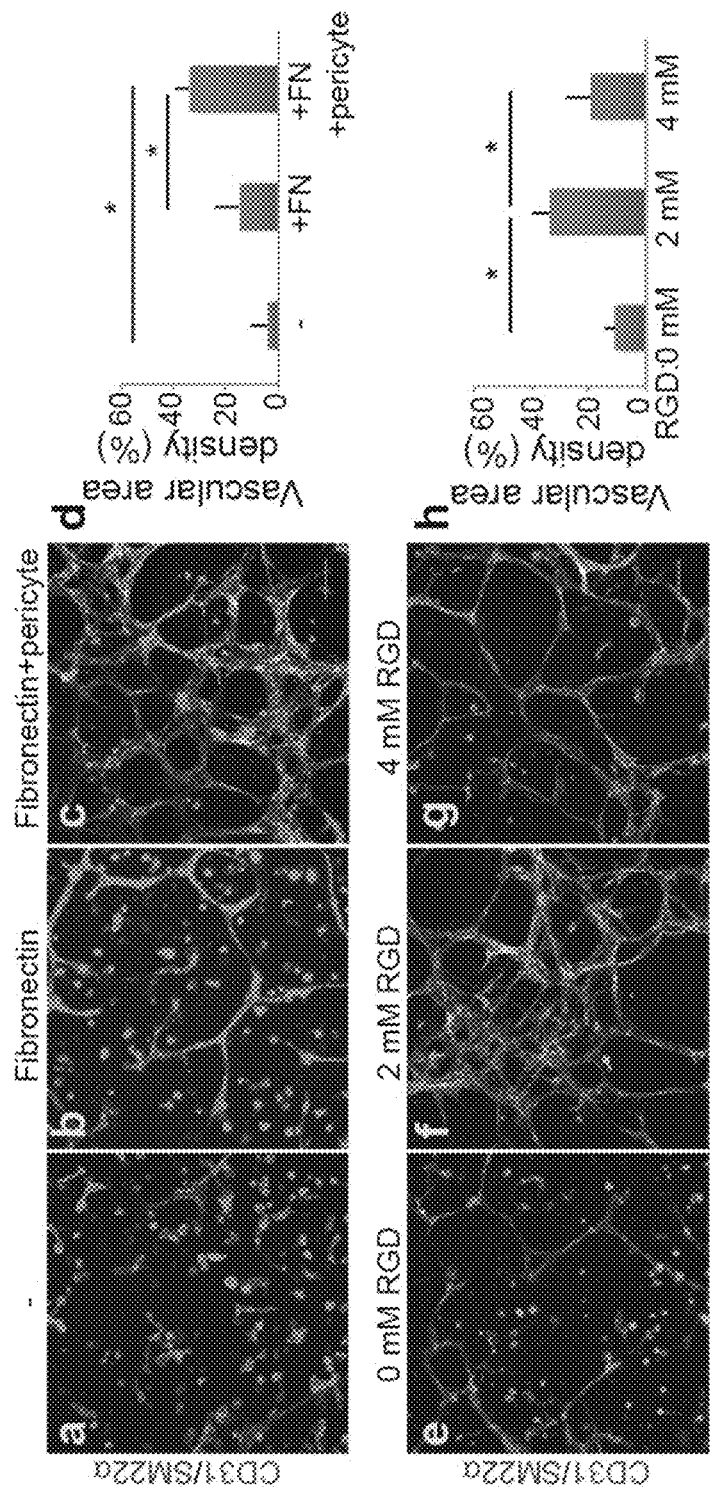
FIGS. 2A-2P demonstrate further optimization of multiple components to engineer capillary beds in synthetic PEG gels. (A-C) ECs were cultured in PEG gel (45% cross-linking with 2 mM RGD), with or without fibronectin or pericyte. CD31$^+$ ECs (green) and SM22α$^+$ pericytes (purple) are labeled. "−" indicates ECs; "+FN" indicates ECs+fibronectin. In (E-G), different concentrations of RGD were used. EC-pericytes were co-cultured in 45% cross-linked hydrogels with fibronectin. In (I-K), gel stiffness was varied. EC-pericytes were co-cultured in 2 mM RGD hydrogels with fibronectin. 35%/45%/60% of the norbornene group was cross-linked by MMP-sensitive peptide to modulate gel stiffness. (D, H, L) The vascular area density (the ratio of vascular covered area to total area) was measured by Nikon NIS element. Data represent mean±SD (n>=3), *:p<0.05. In (M-O), EC-pericytes were co-cultured in 2 mM RGD, 50% cross-linked hydrogels with fibronectin at different time point. (M'-O') Higher magnification of M-P. Scale Bar: 100 μm. Note: Hydrogels of (A-I) were formed at the bottom of 24-well plate while hydrogels of (M-P) were formed in a transwell insert to improve nutrient diffusion. (P) Clustering analysis of RNA-seq data (TPM) was generated by clustering algorithm of Galaxy (Distance of matrix: Pearson correlation, type of linkage: average).

We first investigated roles for individual components of the 3D microenvironment during vascular network formation, including soluble (fibronectin, FN), insoluble (CRGDS), mechanical (matrix crosslinking density), and cellular (pericytes) factors. Limited cellular organization was observed for ECs cultured in media without FN (FIG. 2a), while the addition of soluble FN induced vascular network formation (FIG. 2b). Interconnected vascular networks were pronounced when ECs were cocultured with pericytes in sECM, leading to a quantitative increase in vascular area density (FIGS. 2d-h). Matrix properties played an important role in vascular organization in sECM, as network formation was minimal in the absence of RGD, while the highest vascular coverage was observed for intermediate RGD concentrations (FIGS. 2e-h, constant 45% crosslinking) and matrix crosslinking density (FIG. 2i-l); constant 2 mM RGD). Finally, vascular networks persisted for at least 16 days when cultured using our optimized conditions (FIGS. 2m-p). Thus, vascular network formation was optimal when ECs were cocultured with pericytes in sECM and could be tuned by changing cell adhesion ligand density or matrix mechanical properties of the synthetic scaffold.

We performed RNA-sequencing (RNA-seq) to compare global gene expression of cells cultured in sECM versus standard 2D and 3D platforms using two-dimensional clustering and Spearman's pairwise rank correlation (FIG. 2p). Global gene expression was highly correlated for EC-pericyte cocultures in sECM vs. Matrigel (Spearman's correlation, $\rho=0.98$-$0.99$), with comparisons at both days 1 and 3 being approximately equivalent to expected correlation between biological replicates. Individual cell types were also highly correlated for 3D monocultures in sECM at different time points ($\rho \sim 0.97$-$0.98$; days 1 vs 3), but were less correlated when comparing 2D cultured on TCP and 3D culture in sECM ($\rho \sim 0.95$) (FIG. 2p, further discussed below). Together, our results demonstrate that a defined sECM provides the necessary cues to model global 3D vascular function similarly to Matrigel; the gold standard material for vasculogenesis[16].

We further investigated 3D vascular network formation by EBseq[31] analysis (FDR≤0.005) to analyze differential gene expression. We identified cell type-specific mechanisms that mediated 3D vascular network formation in sECM by identifying characteristic gene expression profiles for ECs and pericytes in 3D culture. We gained further insight into functional characteristics for ECs and pericytes in 3D culture by using DAVID Gene Ontology (GO) Functional Classification[32] (GOTERM_BP_FAT algorithm) to identify functional gene signatures. ECs and pericytes distinctly expressed a wide range of genes associated with blood vessel formation[8,33-36], including vasculature development, cell-matrix adhesion (e.g., integrins), ECM components (e.g., collagen and laminin), and proteases (e.g., MMPs). Characteristic genes included cell-type specific growth factor-receptor pairs known to be important for blood vessel formation and stabilization, such as EC enrichment for KDR (VEGFR2), PDGFA, PDGFB, HBEGF, and CXCR4, and pericyte enrichment for the complementary genes VEGFA, PDGFRA, PDGFRB, EGFR (also ERBB2/EGFR-2), and CXCL12/SDF-1 (GF-Receptor genes)[8,33-35]. In total, we identified 583 genes enriched in ECs (relative to pericytes) and 640 genes enriched in pericytes (relative to ECs) in 3D sECM for both days 1 and 3.

Further analysis of specific gene sets for ECs and pericytes suggested distinct roles for remodeling the ECM during vascular network formation. ECs and pericytes each expressed ECM isoforms associated with basement membrane assembly including collagen IV and laminin, which are localized on vascular networks formed within PEG hydrogels[21]. However, our results suggested that pericytes played a predominant role for producing collagens I and III, as COL1A1, COL1A2, and COL3A1 isoforms were each characterized by >25-fold higher expression than ECs at days 1 and 3. Pericytes were also characterized by enhanced expression for genes implicated in collagen I and III matrix assembly, including >70-fold higher fibronectin (FN1) expression and >5-fold higher α11-integrin expression, an integrin implicated in remodeling[37,38], but which to the best of our knowledge has not been specifically investigated for a role during blood vessel formation. Further, pericytes were characterized by enriched α10-integrin and its receptors collagen IV (several isoforms; also expressed by ECs), collagen VI (COL6A1, COL6A2, and COL6A3; pericyte-enriched), and laminin-1 (LAMA1, LAMB1, LAMC1; pericyte-enriched)[39]. Finally, α9-integrin plays a role during angiogenesis by binding VEGFA and thrombospondin-1 (THSD1)[40,41], each of which was enriched for EC gene expression. Taken together, these results demonstrate the value of a fully defined 3D vascular model and global gene expression profiling for identifying relationships between ECs and pericytes.

Engineered materials that mimic the extracellular matrix (ECM) have played an increasing role in deconstructing the 3D microenvironment by providing strict control over biochemical and biophysical properties[28], and several approaches to investigate and promote blood vessel formation have been reported.[4,16-18] To investigate cellular and extracellular influences on 3D vascular network formation, we fabricated a synthetic extracellular matrix (sECM) permissive towards cellular remodeling using "thiol-ene" chemistry[19,24] to crosslink 8-arm poly (ethylene glycol) (PEG) molecules with MMP-degradable peptides[29] and to incorporate pendant RGD (Arg-Gly-Asp)-containing peptides for cell adhesion[30]. We then compared global gene expression for cells cultured in sECM to tissue culture polystyrene (TCP) and Matrigel, which are common 2D and 3D in vitro culture formats for investigating vascular biology.

Due to the differences in clustering for 2D compared to 3D monocultures (FIG. 2p), we further analyzed differential gene expression for ECs cultured in sECM (3D culture) or on TCP (2D culture), and identified "GO" functional terms using DAVID[32,42]. Genes related to vascular morphogenesis and remodeling were upregulated in 3D culture[8,33-35], including cell adhesion genes (e.g., GO:0007155~cell adhesion; 49 genes), cell migration genes (e.g., GO:0006928~cell motion; 34 genes), and blood vessel morphogenesis genes (e.g., GO:0001944~vasculature development; 23 genes). In contrast, ECs were primarily characterized by higher expression of proliferation genes in 2D compared to 3D culture, as 9 out of the top 10 upregulated gene sets were cell cycle-related. These data demonstrate that vascular networks can form in chemically defined materials with minimal components and provide insights into how materials instruct tissue modeling.

Figures 3A, 3B, 3C, 3D, 3E, 3F:
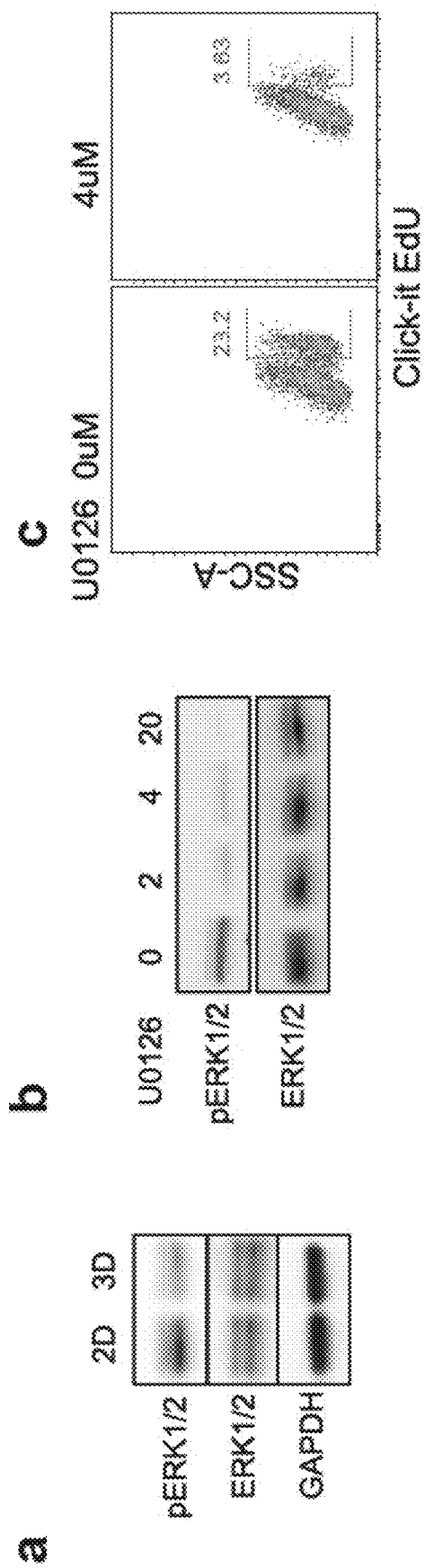
FIGS. 3A-3F present data demonstrating that the ERK pathway modulates EC response to 3D microenvironment. (A) Western blot showed ERK activity in 2D and 3D culture. (B) Western blot showed U0126 decreased ERK activity. (C) Click-it EdU assay showed U0126 treatment decreased EC proliferation. (D) Top 10 (TPM>100, top 10 fold change) vasculature (TPM>100, Top 10 fold change) (AmiGO, GO:0001944) and cell cycle genes (AmiGO, GO:0007049) from RNA-seq. Full gene list of vasculature and cell cycle was generated by Amigo. (E) RT-qPCR revealed that inhibition of ERK pathway increased vasculature gene expression but suppressed cell cycle gene expression. Data was normalized to DMSO control (not shown). (F) RT-qPCR demonstrated that knockdown ERK2 by SiRNA enhanced vasculature gene expression and suppressed cell cycle gene expression. Data was normalized to NT control. ERK2i, siRNA of ERK2. NT, non-targeting.

We investigated a potential role for ERK signaling on cell cycle gene expression for ECs cultured on TCP surfaces since ERK regulates EC functions that include proliferation, blood vessel morphogenesis, and mechanotransduction[34,35,43-46]. Phosphorylated ERK1/2 (pERK1/2) was higher for ECs on TCP compared to cells cultured in sECM (FIG. 3A), which demonstrates that ERK activity was increased when using the standard 2D culture platform. We further investigated the role for ERK activity in regulating the shift to a proliferative phenotype by comparing the top 10 enriched cycle genes from 2D culture and vascular development genes from 3D culture (Day 3) for ECs on TCP after pERK inhibition (FIGS. 3b-d). ECs on TCP were first treated with the MEK inhibitor U0126 (an upstream regulator of ERK phosphorylation), which reduced proliferation and decreased the expression of cell cycle genes in a dose-dependent manner (10 of 10 genes downregulated) (FIGS. 3b-c). The reduction in cell cycle gene expression correlated to increased expression of 3D-like vascular development genes for ECs on TCP (8 of 10 genes upregulated; FIG. 3e). Reduced cell cycle and increased vascular development gene expression was observed when ERK2 was silenced by RNAi (FIG. 3f), which confirms results using MEK inhibitor to reduce ERK signaling. These combined results suggest that over-activation of ERK signaling disrupts the expression of vascular development genes and induces a proliferative phenotype for ECs cultured on TCP.

Figures 5A, 5B, 5C, 5D:
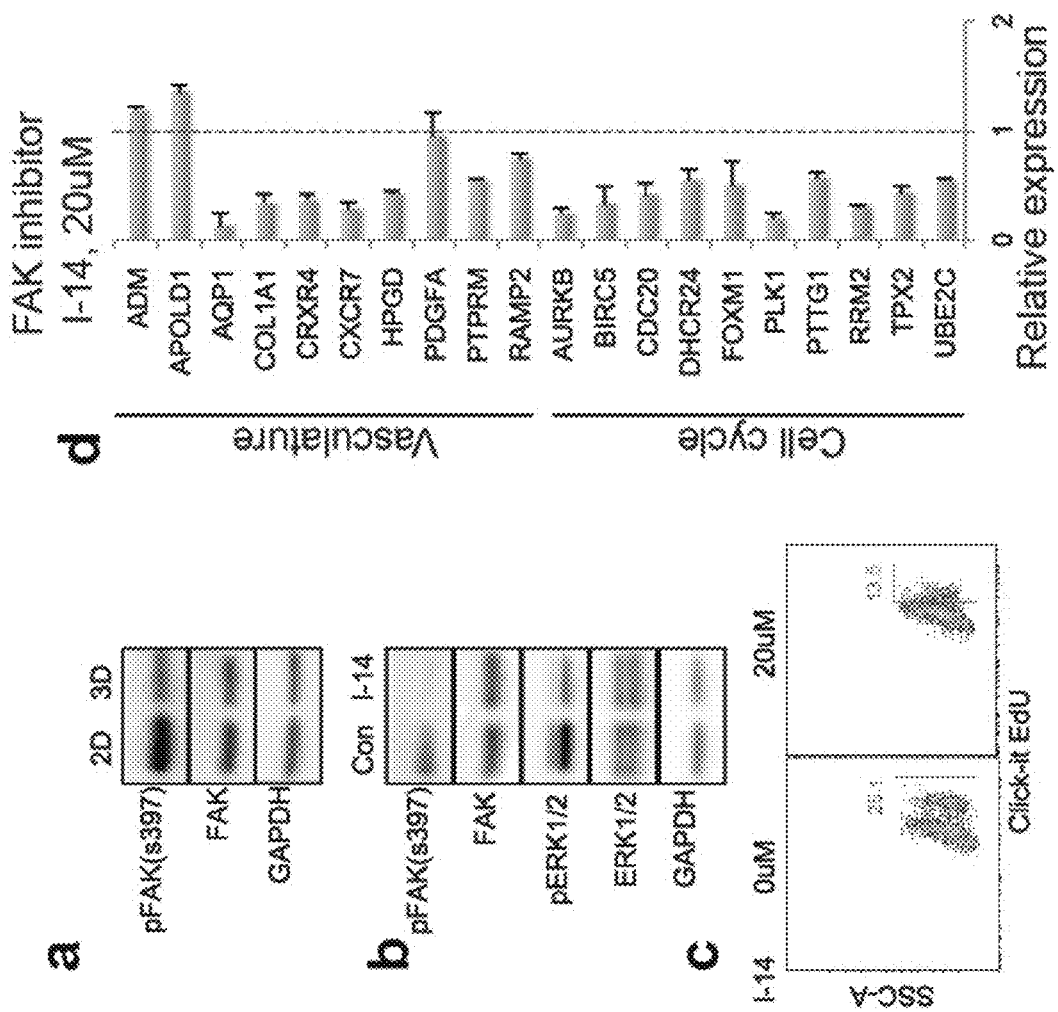
FIGS. 5A-5D presents FAK pathway data. (A) Western blot showed FAK activity in 2D and 3D culture. (B) Western blot showed inhibition of FAK activity by 20 μM Inhibitor-14 ("I-14") treatment. (C) I-14 suppressed cell proliferation. (D) RT-qPCR revealed I-14 treatment decreased both vasculature and cell cycle gene expression.
Figure 6:
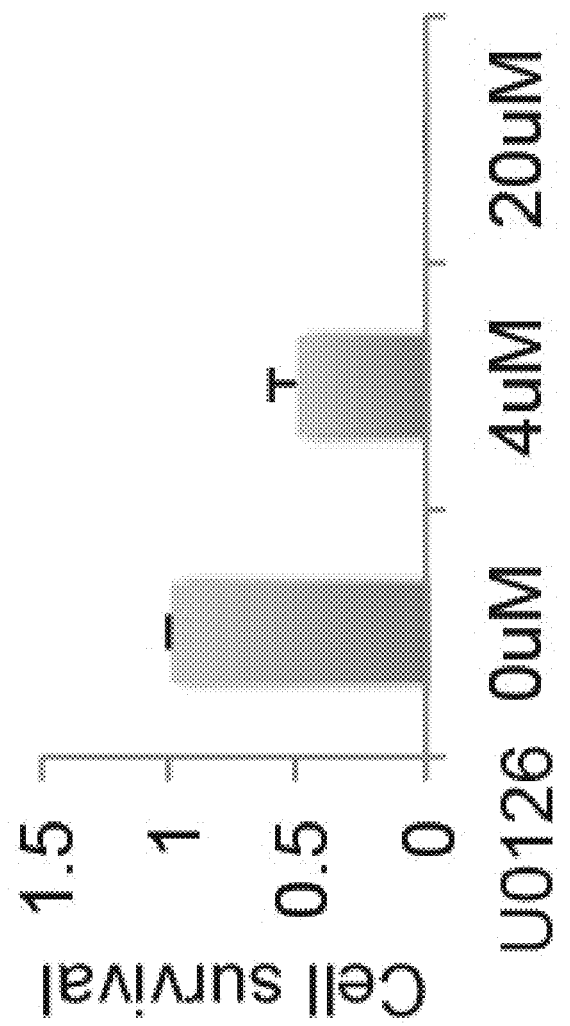
FIG. 6 depicts endothelial cell survival upon U0126 treatment in two-dimensional (2D) culture.
Figure 7:
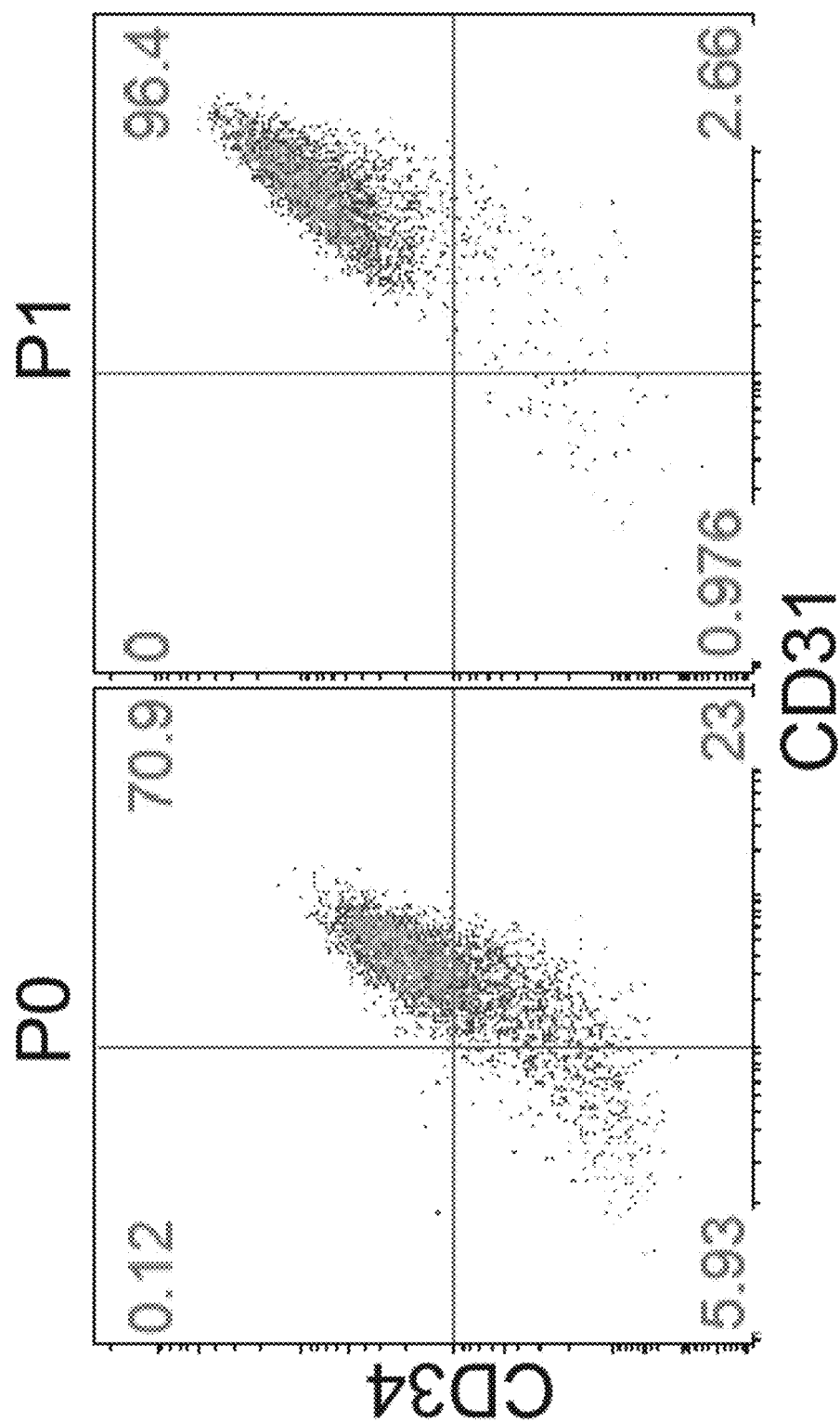
FIG. 7 demonstrates improved endothelial cell purity following passaging. P0: the human pluripotent stem cells underwent endothelial cell differentiation for five days. P1: the differentiated endothelial cells were passaged and cultured in E7V media for another two to three days.

Cells cultured on TCP are exposed to a non-physiological planar surface and a modulus that is orders of magnitude higher than most tissues[47,48], which is notable since matrix mechanical properties regulate proliferation through a focal adhesion kinase (FAK)-ERK signaling loop for 2D and 3D culture[43,49]. Increased pFAK expression was observed for ECs on TCP (FIG. 5a), while the pFAK inhibitor I-14 reduced pERK expression and proliferation (FIGS. 5b-c). However, FAK inhibition had only limited effect on 3D-like vascular genes (FIG. 5d), which differs from the influence of ERK inhibition (FIG. 3). Therefore, our results support a role for FAK-ERK signaling in mediating mechanical cues that regulate proliferation[49-51], but suggest that the influence of ERK on vascular expression is regulated by FAK-independent signaling. Complete inhibition of ERK activity induced cell death for ECs on TCP (FIG. 6), which is consistent with previous results demonstrating that blocking ERK induces apoptosis[44,45] and that ERK is a positive regulator of vascular function[43,44]. These combined results indicate that moderate ERK signaling is required for EC survival and vascular gene expression, but that overexpressed ERK (such as on TCP surfaces) induces a shift to a proliferative phenotype that disrupts normal vascular function.

REFERENCES

1 Takebe, T. et al. Vascularized and functional human liver from an iPSC-derived organ bud transplant. *Nature* 499, 481-484, doi:10.1038/nature12271 (2013).
2 Nakano, T. et al. Self-formation of optic cups and storable stratified neural retina from human ESCs. *Cell Stem Cell* 10, 771-785, doi:10.1016/j.stem.2012.05.009 (2012).
3 Lancaster, M. A. et al. Cerebral organoids model human brain development and microcephaly. *Nature* 501, 373-379, doi:10.1038/nature12517 (2013).
4 Hughes, C. S., Postovit, L. M. & Lajoie, G. A. Matrigel: A complex protein mixture required for optimal growth of cell culture. *Proteomics* 10, 1886-1890, doi:10.1002/pmic.200900758 (2010).
5 Hughes, C. S., Radan, L., Betts, D., Postovit, L. M. & Lajoie, G. A. Proteomic analysis of extracellular matrices used in stem cell culture. *Proteomics* 11, 3983-3991, doi:10.1002/pmic.201100030 (2011).
6 Novosel, E. C., Kleinhans, C. & Kluger, P. J. Vascularization is the key challenge in tissue engineering. *Adv. Drug Deliv. Rev.* 63, 300-311 (2011).
7 Phelps, E. A. & García, A. J. Engineering more than a cell: vascularization strategies in tissue engineering. *Curr. Opin. Biotechnol.* 21, 704-709 (2010).
8 Stratman, A. N. & Davis, G. E. Endothelial Cell-Pericyte Interactions Stimulate Basement Membrane Matrix Assembly: Influence on Vascular Tube Remodeling, Maturation, and Stabilization. *Microsc. microanal.* 18, 68-80 (2012).
9 Descamps, B. & Emanueli, C. Vascular differentiation from embryonic stem cells: Novel technologies and therapeutic promises. *Vascul Pharmacol* 56, 267-279, doi:10.1016/j.vph.2012.03.007 (2012).
10 Park, T. S. et al. Vascular Progenitors From Cord Blood-Derived Induced Pluripotent Stem Cells Possess Augmented Capacity for Regenerating Ischemic Retinal Vasculature. *Circulation* 129, 359-372, doi:10.1161/circulationaha.113.003000 (2014).
11 White, M. P. et al. Limited Gene Expression Variation in Human Embryonic Stem Cell and Induced Pluripotent Stem Cell-Derived Endothelial Cells. *Stem Cells* 31, 92-103, doi:10.1002/stem.1267 (2013).
12 Salvagiotto, G. et al. A Defined, Feeder-Free, Serum-Free System to Generate In Vitro Hematopoietic Progenitors and Differentiated Blood Cells from hESCs and hiPSCs. *PLoS One* 6, doi:e17829 (2011).
13 James, D. et al. Expansion and maintenance of human embryonic stem cell-derived endothelial cells by TGF [beta] inhibition is Id1 dependent. *Nat Biotech* 28, 161-166 (2010).
14 Wang, Z. Z. et al. Endothelial cells derived from human embryonic stem cells form durable blood vessels in vivo. *Nat Biotechnol* 25, 317-318 (2007).
15 Levenberg, S., Golub, J. S., Amit, M., Itskovitz-Eldor, J. & Langer, R. Endothelial cells derived from human embryonic stem cells. *Proc Natl Acad Sci USA* 99, 4391-4396, doi:10.1073/pnas.032074999 (2002).
16 Kleinman, H. K. & Martin, G. R. Matrigel: Basement membrane matrix with biological activity. *Semin Cancer Biol* 15, 378-386, doi:10.1016/j.semcancer.2005.05.004 (2005).

17 Vukicevic, S. et al. IDENTIFICATION OF MULTIPLE ACTIVE GROWTH-FACTORS IN BASEMENT-MEMBRANE MATRIGEL SUGGESTS CAUTION IN INTERPRETATION OF CELLULAR-ACTIVITY RELATED TO EXTRACELLULAR-MATRIX COMPONENTS. *Exp Cell Res* 202, 1-8, doi:10.1016/0014-4827(92)90397-q (1992).

18 Yang, Y. L., Leone, L. M. & Kaufman, L. J. Elastic Moduli of Collagen Gels Can Be Predicted from Two-Dimensional Confocal Microscopy. *Biophys J* 97, 2051-2060 (2009).

19 Nguyen, E. H., Zanotelli, M. R., Schwartz, M. P. & Murphy, W. L. Differential effects of cell adhesion, modulus and VEGFR-2 inhibition on capillary network formation in synthetic hydrogel arrays. *Biomaterials* 35, 2149-2161, (2014).

Kusuma, S. et al. Self-organized vascular networks from human pluripotent stem cells in a synthetic matrix. *Proceedings of the National Academy of Sciences* 110, 12601-12606, doi:10.1073/pnas.1306562110 (2013).

21 Moon, J. J. et al. Biomimetic hydrogels with pro-angiogenic properties. *Biomaterials* 31, 3840-3847, doi:10.1016/j.biomaterials.2010.01.104 (2010).

22 Phelps, E. A., Landázuri, N., Thulé, P. M., Taylor, W. R. & Garcia, A. J. Bioartificial matrices for therapeutic vascularization. *Proceedings of the National Academy of Sciences*, doi:10.1073/pnas.0905447107 (2009).

23 Vickerman, V., Blundo, J., Chung, S. & Kamm, R. Design, fabrication and implementation of a novel multi-parameter control microfluidic platform for three-dimensional cell culture and real-time imaging. *Lab Chip* 8, 1468-1477, doi:10.1039/b802395f (2008).

24 Fairbanks, B. D. et al. A Versatile Synthetic Extracellular Matrix Mimic via Thiol-Norbornene Photopolymerization. *Adv Mater* 21, 5005-5010 (2009).

25 Yu, P. Z., Pan, G. J., Yu, J. Y. & Thomson, J. A. FGF2 Sustains NANOG and Switches the Outcome of BMP4-Induced Human Embryonic Stem Cell Differentiation. *Cell Stem Cell* 8, 326-334 (2011).

26 Chen, G. K. et al. Chemically defined conditions for human iPSC derivation and culture. *Nat. Methods* 8, 424-U476 (2011).

27 Lei, T. et al. Xeno-free derivation and culture of human embryonic stem cells: current status, problems and challenges. *Cell Res* 17, 682-688 (2007).

28 Lutolf, M. P., Gilbert, P. M. & Blau, H. M. Designing materials to direct stem-cell fate. *Nature* 462, 433-441, doi:10.1038/nature08602 (2009).

29 Nagase, H. & Fields, G. B. Human matrix metalloproteinase specificity studies using collagen sequence-based synthetic peptides. *Biopolymers* 40, 399-416 (1996).

30 Pierschbacher, M. D. & Ruoslahti, E. Cell attachment activity of fibronectin can be duplicated by small synthetic fragments of the molecule. *Nature* 309, 30-33 (1984).

31 Leng, N. et al. EBSeq: an empirical Bayes hierarchical model for inference in RNA-seq experiments. *Bioinformatics* 29, 1035-1043, doi:10.1093/bioinformatics/btt087 (2013).

32 Huang, D. W., Sherman, B. T. & Lempicki, R. A. Systematic and integrative analysis of large gene lists using DAVID bioinformatics resources. *Nat. Protocols* 4, 44-57, (2008).

33 Herbert, S. P. & Stainier, D. Y. R. Molecular control of endothelial cell behaviour during blood vessel morphogenesis. *Nat. Rev. Mol. Cell Biol.* 12, 551-564, doi:10.1038/nrm3176 (2011).

34 Niland, S. & Eble, J. A. Integrin-Mediated Cell-Matrix Interaction in Physiological and Pathological Blood Vessel Formation. *Journal of Oncology* 2012, 25, doi:10.1155/2012/125278 (2012).

35 Ramjaun, A. R. & Hodivala-Dilke, K. The role of cell adhesion pathways in angiogenesis. *Int J Biochem Cell Biol* 41, 521-530 (2009).

36 Bell, S. E. et al. Differential gene expression during capillary morphogenesis in 3D collagen matrices: regulated expression of genes involved in basement membrane matrix assembly, cell cycle progression, cellular differentiation and G-protein signaling. *J Cell Sci* 114, 2755-2773 (2001).

37 Svendsen, Ø. S. et al. The $\alpha 11\beta 1$ Integrin Has a Mechanistic Role in Control of Interstitial Fluid Pressure and Edema Formation in Inflammation. *Arterioscler Thromb Vasc Biol* 29, 1864-1870, doi:10.1161/atvbaha.109.194308 (2009).

38 Velling, T., Risteli, J., Wennerberg, K., Mosher, D. F. & Johansson, S. Polymerization of Type I and III Collagens Is Dependent On Fibronectin and Enhanced By Integrins $\alpha 11\beta 1$ and $\alpha 2\beta 1$. *Journal of Biological Chemistry* 277, 37377-37381 (2002).

39 Tulla, M. et al. Selective Binding of Collagen Subtypes by Integrin $\alpha 1$I, $\alpha 2$I, and $\alpha 10$I Domains. *J. Biol. Chem.* 276, 48206-48212, (2001).

40 Vlahakis, N. E. et al. Integrin alpha 9 beta 1 directly binds to vascular endothelial growth factor (VEGF)-a and contributes to VEGF-A-induced angiogenesis. *J. Biol. Chem.* 282, 15187-15196, doi:10.1074/jbc.M609323200 (2007).

41 Staniszewska, I. et al. Interaction of alpha 9 beta 1 integrin with thrombospondin-1 promotes angiogenesis. *Circ Res* 100, 1308-1316, doi:10.1161/01.res.0000266662.98355.66 (2007).

42 Huang, D. W., Sherman, B. T. & Lempicki, R. A. Bioinformatics enrichment tools: paths toward the comprehensive functional analysis of large gene lists. *Nucleic Acids Res.* 37, 1-13, doi:10.1093/nar/gkn923 (2009).

43 Deng, Y. et al. Endothelial RAF 1/ERK activation regulates arterial morphogenesis. *Blood* 121, 3988-3996, doi:10.1182/blood-2012-12-474601 (2013).

44 Yang, B. H., Cao, D. J., Sainz, I., Colman, R. W. & Guo, Y. L. Different roles of ERK and p38 MAP kinases during tube formation from endothelial cells cultured in 3-dimensional collagen matrices. *J. Cell. Physiol.* 200, 360-369, doi:10.1002/jcp.20025 (2004).

45 Ilan, N., Mahooti, S. & Madri, J. A. Distinct signal transduction pathways are utilized during the tube formation and survival phases of in vitro angiogenesis. *J Cell Sci* 111 (Pt 24), 3621-3631 (1998).

46 Chien, S., Li, S. & Shyy, J. Y. J. Effects of mechanical forces on signal transduction and gene expression in endothelial cells. *Hypertension* 31, 162-169 (1998).

47 Cox, T. R. & Erler, J. T. Remodeling and homeostasis of the extracellular matrix: implications for fibrotic diseases and cancer. *Dis. Model. Mech.* 4, 165-178, doi:10.1242/dmm.004077 (2011).

48 Miyake, K., Satomi, N. & Sasaki, S. Elastic modulus of polystyrene film from near surface to bulk measured by nanoindentation using atomic force microscopy. *Appl. Phys. Lett.* 89, (2006).

49 Provenzano, P. P., Inman, D. R., Eliceiri, K. W. & Keely, P. J. Matrix density-induced mechanoregulation of breast cell phenotype, signaling and gene expression through a FAK-ERK linkage. *Oncogene* 28, 4326-4343, (2009).

50 Provenzano, P. P. & Keely, P. J. Mechanical signaling through the cytoskeleton regulates cell proliferation by coordinated focal adhesion and Rho GTPase signaling. *J. Cell Sci.* 124, 1195-1205 (2011).

51 Paszek, M. J. et al. Tensional homeostasis and the malignant phenotype. *Cancer Cell* 8, 241-254 (2005).

We claim:

1. A method of producing human endothelial cells, wherein the method comprises
    (i) culturing human pluripotent stem cells on a substrate on day 0 in a chemically defined, xenogeneic material-free, serum-free, albumin-free, culture medium comprising insulin, transferrin, Transforming Growth Factor Beta 1 (TGFβ1), Fibroblast Growth Factor 2 (FGF2), bone morphogenetic protein 4 (BMP4), and Activin A such that Brachyury-positive mesodermal cells are obtained on day 2; and
    (ii) replacing the media of the mesodermal cells on day 2 with a chemically defined, xenogeneic material-free, serum-free, albumin-free, culture medium that comprises insulin and Vascular Endothelial Growth Factor (VEGF) and does not comprise Fibroblast Growth Factor 2 (FGF2) and culturing the cells such that a cell population comprising at least 50% CD31+ human endothelial cells is obtained on day 5.

2. The method of claim 1, wherein the culture medium of (ii) further comprises an inhibitor of TGFβ1-mediated signaling.

3. The method of claim 2, wherein the inhibitor of TGFβ1-mediated signaling is selected from the group consisting of SB431542 and A-83-01.

4. The method of claim 3, wherein the cell population on obtained day 5 comprises at least 75% CD31$^+$ endothelial cells.

5. The method of claim 1, wherein the cell population comprises at least 50% CD31$^+$/CD34$^+$ endothelial cells obtained on day 5.

6. The method of claim 1, wherein the chemically defined culture medium of (i) further comprises a ROCK inhibitor.

7. The method of claim 6, wherein the ROCK inhibitor is selected from the group consisting of Y-27632, Blebbistatin, and HA-1077.

8. The method of claim 1, wherein the substrate comprises vitronectin.

9. The method of claim 8, wherein the vitronectin is recombinant human vitronectin.

10. The method of claim 2, wherein the chemically defined culture medium of (ii) additionally comprises a factor selected from the group consisting of BMP4, BMP2, and BMP7.

11. A method of producing human endothelial cells, wherein the method comprises:
    (i) culturing human pluripotent stem cells on a substrate on day 0 in a chemically defined, xenogeneic material-free, serum-free, albumin-free, culture medium comprising insulin, transferrin, Transforming Growth Factor Beta 1 (TGFβ1), Fibroblast Growth Factor 2 (FGF2), bone morphogenetic protein 4 (BMP4), and Activin A such that Brachyury-positive mesodermal cells are obtained on day 2; and
    (ii) replacing the media of the mesodermal cells on day 2 with a chemically defined, xenogeneic material-free, serum-free, albumin-free, culture medium that comprises insulin and a growth factor wherein the growth factor is Vascular Endothelial Growth Factor (VEGF) or FGF and culturing the cells such that a cell population of human endothelial cells is obtained on day 5.

12. The method of claim 11, wherein the cell population of human endothelial cells comprises at least 30% CD31+ cells.

* * * * *